United States Patent
Kroon et al.

(10) Patent No.: US 10,064,805 B2
(45) Date of Patent: Sep. 4, 2018

(54) PERSONAL CARE COMPOSITION FOR A KERATIN SUBSTRATE COMPRISING CONDITIONING AND/OR STYLING POLYMER

(71) Applicant: HERCULES INNCORPORATED, Wilmington, DE (US)

(72) Inventors: Gijsbert Kroon, Giessendam (NL); Amna Khatun, West Yorkshire (GB); Tuttu Maria Nuutinen, Delft (NL); Michael Franzke, Barendrecht (NL)

(73) Assignee: HERCULES LLC, Wilmington, DE (US)

( * ) Notice: Subject to any disclaimer, the term of this patent is extended or adjusted under 35 U.S.C. 154(b) by 0 days.

(21) Appl. No.: 15/308,375

(22) PCT Filed: May 4, 2015

(86) PCT No.: PCT/US2015/029006
§ 371 (c)(1),
(2) Date: Nov. 2, 2016

(87) PCT Pub. No.: WO2016/178660
PCT Pub. Date: Nov. 10, 2016

(65) Prior Publication Data
US 2017/0266096 A1     Sep. 21, 2017

Related U.S. Application Data

(60) Provisional application No. 61/987,764, filed on May 2, 2014.

(51) Int. Cl.
*A61K 8/00* (2006.01)
*A61K 8/81* (2006.01)
(Continued)

(52) U.S. Cl.
CPC ............ *A61K 8/817* (2013.01); *A61K 8/8147* (2013.01); *A61K 8/8152* (2013.01);
(Continued)

(58) Field of Classification Search
None
See application file for complete search history.

(56) References Cited

U.S. PATENT DOCUMENTS

2004/0241130 A1   12/2004   Tamareselvy et al.
2007/0148116 A1*   6/2007   Seigneurin ............... A61K 8/39
                                              424/70.12
(Continued)

FOREIGN PATENT DOCUMENTS

WO      2007090554 A1    8/2007

OTHER PUBLICATIONS

International Search Reportt of PCT Application No. PCT/US15/29006 filed on May 4, 2015.

*Primary Examiner* — Brian Gulledge
(74) *Attorney, Agent, or Firm* — William J. Davis; Nathalie Tietcheu

(57) ABSTRACT

A personal care conditioning and/or styling composition for a keratin substrate comprising: (A) at least one conditioning and/or styling ter/tetra polymer obtained by polymerizing: (i) about 50 wt. % to 97 wt. % of at least one cationic or pseudo-cationic monomer selected from the group consisting of diallyl dimethyl ammonium chloride (DADMAC), Hydroxyethyl-pyrrolidone-methacrylate (MO6), and/or Vinylpyrrolidone (VP); (ii) about 1 wt. % to 30 wt. % of at least one anionic monomer selected from the group consisting of (a) acrylic acid (AA), (b) acrylamido methylpropyl sulfonate (AMPS), and/or (c) sodium methyl allyl sulfonate (SMAS); and (iii) about 0.1 wt. % to 20 wt. % of at least one hydrophobic monomer selected from the group consisting of
(Continued)

(a) polyoxyethylene (PEG)-18-behenylether-methacrylate (BEM) (b) Lauryl-ethoxylated-methacrylate (LEM), (c) stearyl acrylate (SA), (d) Streath-10-allyl-ether, and/or (e) Vinylcaprolactam (V-cap); and wherein said ter/tetra polymer has a cationic degree of substitution (Cat-DS) of greater than about 0.001 units, and wherein the cationic charge density is in the range of about 1 meq/g to about 6.5 meq/g; (B) at least one cosmetically acceptable excipient; and (C) optionally, at least one effective amount of personal care active ingredient. Also, disclosed is a process of preparing said ter/tetra polymer, and its method of use.

9 Claims, 4 Drawing Sheets

(51) Int. Cl.
*A61Q 5/12* (2006.01)
*A61Q 5/06* (2006.01)
*A61Q 5/02* (2006.01)
*A61Q 5/00* (2006.01)

(52) U.S. Cl.
CPC ............ *A61K 8/8182* (2013.01); *A61Q 5/004* (2013.01); *A61Q 5/02* (2013.01); *A61Q 5/06* (2013.01); *A61Q 5/12* (2013.01); *A61K 2800/5426* (2013.01)

(56) References Cited

U.S. PATENT DOCUMENTS

| | | |
|---|---|---|
| 2008/0096786 A1* | 4/2008 | Holt ................... C11D 3/3773 510/275 |
| 2008/0311066 A1 | 12/2008 | Sarmain et al. |
| 2010/0166813 A1 | 7/2010 | Hall et al. |
| 2010/0179082 A1 | 7/2010 | Castro et al. |
| 2011/0189248 A1 | 8/2011 | Baldaro et al. |
| 2011/0318285 A1 | 12/2011 | Erazo-Majewick et al. |

* cited by examiner

PERSONAL CARE COMPOSITION FOR A KERATIN SUBSTRATE COMPRISING CONDITIONING AND/OR STYLING POLYMER

FIELD OF THE INVENTION

The present application relates to a personal care composition, and, more particularly, to a personal care composition comprising a conditioning and/or styling copolymer for a keratin substrate of hair and/or skin origin.

BACKGROUND OF THE INVENTION

Undamaged virgin hair is smooth and shiny; its cuticles on the surface of the hair lie down smoothly making the combing easy. The hair surface is also hydrophobic in nature preventing excessive water absorption during washing. When the hair is either mechanically damaged through back combing, heavy brushing, or chemically damaged through bleaching, perming or coloring, the hair surface becomes rough and frizzy and difficult to detangle and comb. As the hair surface becomes more hydrophilic, the resulting hair fibers swell during washing, making the hair even more difficult to comb.

Current conditioning and/or styling systems for regular and damaged hair generally use one or more combinations of cationic surfactants, amphoteric surfactants, silicones, fatty alcohols, polyquaterniums, amino acids, proteins, lipids and humectants. Wet conditioning of regular or damaged hair is accomplished by neutralizing the anionic charge of the hair by positively charged surfactants and polymers and creating a hydrophobic layer from surfactant and polymers. This hydrophobic layer results in a reduction of the swelling of the hair fibers by making the hair more hydrophobic and smoothening the cuticle layers thus and reducing friction of the hair fibers. An overall result of wet conditioning is improved detangling, manageability and soft feel of the hair. Upon treatment with cleansing systems like shampoos, 2/1 shampoos, body washes or shower gels, the combing performance, detangling properties, hydrophobicity of the hair and lubricity are not maintained sufficiently.

U.S. Publication Number 20060217285 discloses a controlled structure copolymer comprising at least two different parts, a first part A, amphoteric or zwitterionic, including anionic or potentially anionic units, and cationic or potentially cationic units, or zwitterionic units, and another part B, non amphoteric or zwitterionic. Said copolymer further exhibits a high potential for adaptation, through variation in its composition, in order to improve or modify the properties of compositions in which it is introduced.

U.S. Publication Number 20060217285 assigned to Rhodia discloses a concentrated ingredient for treating and/or modifying surfaces, especially for treating and/or modifying the skin and/or the hair. The invention also relates to the use of this ingredient in cosmetic compositions, for example in shampoos, shower gels or leave-in or rinse-out hair conditioners. The ingredient comprises a conditioning agent and a polymer for aiding deposition.

U.S. Publication No. 20060217285 assigned to Rhodia discloses compositions for household care which include a cationic nanogel, particularly for treating and/or modifying hard or textile surfaces. The composition particularly enables a hydrophilization of hard surfaces, particularly useful in cleaning or rinsing operations.

U.S. Pat. No. 7,737,237 assigned to Phodia Chimie discloses a controlled structure copolymer comprising a (block A)-(block B) diblock copolymer, a (block A)-(block B)-(block A) triblock copolymer or a (block B)-(block A)-(block B) triblock copolymer.

U.S. Pat. No. 6,225,429 discloses a process of making a vinyl caprolactam (VCL)-based polymer which comprises suspension polymerizing the monomers in aqueous medium in the absence of an added protective colloid, wherein polymer formed at an early stage of the polymerization functions as a dispersing agent to maintain polymer particles suspended in water throughout the polymerization.

U.S Publication No. 20110003956 assigned to BASF discloses precipitation polymers obtainable by polymerization of a monomer mixture which comprises 30 to 99% by weight of at least one nonionic water-soluble monomer a) and at least one monomer b) different from a) selected from i) monomers carrying at least one hydroxyl group, ii) anionic monomers and iii) mixtures of i) and ii), if appropriate a monomer c) carrying at least one amino group, if appropriate further monomers, where the total amount of a), b), c) and d) is 100% by weight and where the monomer mixture, based on the total amount of a), b), c) and d), comprises less than 0.1% by weight of a monomer with at least 2 free-radically polymerizable double bonds per molecule. The invention furthermore relates to the use of these polymers as rheology modifiers for aqueous compositions, to aqueous compositions comprising these polymers and to the use of the polymers for thickening cosmetic and pharmaceutical preparations.

U.S. Pat. No. 6,451,756 B2 discloses hydrophobically modified polycarboxylate polymers that are useful for promoting soil release from fabrics, particularly cotton and cotton-containing fabrics, by contacting the fabrics with compositions comprising the polymers.

U.S. Pat. No. 6,110,451 assigned to Calgon Coporation discloses a keratin conditioning composition comprising: (a) about 5% to about 50%, by weight, of a surfactant component selected from the group consisting of anionic surfactants, amphoteric surfactants, cationic surfactants, nonionic surfactants, and zwitterionic surfactants; (b) about 0.05% to about 10%, by weight, of a water soluble, organic, ampholytic polymer; (c) about 0.05% to about 10%, by weight, of a water soluble, organic, cationic polymer; (d) zero to about 70%, by weight, of a water insoluble liquid; and (e) an aqueous carrier. The method for treating keratin based substrates according to the present invention comprises contacting the substrate with such composition.

The PCT Publication No. WO2000057847A2 assigned to Calgon Corporation discloses a hair conditioning shampoo composition that contains (a) a surfactant component that can contain anionic surfactants and/or amphoteric surfactants (optionally including zwitterionic and nonionic surfactants), (b) a dispersed, insoluble, nonionic silicone hair conditioning agent, (c) a water soluble, organic, ampholytic polymer hair conditioning agent; and (d) an aqueous carrier. The conditioning shampoo composition optionally contains an organic, water insoluble, liquid component.

U.S. Pat. No. 5,879,670 assigned to Calgon Corporation discloses novel conditioning polymers containing (meth)-acrylamidopropyltrimethyl ammonium chloride, meth (acrylic acid) or 2-(meth)acrylamido-2-methylpropane sulfonic acid and, optionally, a $C_1$-$C_{22}$ alkyl (meth) acrylate and the use thereof in a cosmetically acceptable medium for the treatment of a keratin-containing substrate.

U.S. Publication No. 20110318285 assigned to Hercules Incorporated relates to a personal care composition additive for use on keratin substrates in order to provide long lasting benefits to the keratin substrate such as in conditioning systems, such as 2/1 shampoo's, leave-on and rinse off conditioners, for hair and skin, or for imparting greater water resistance to such personal care compositions as sunscreens or cosmetics.

Therefore, there is an increasing demand for hair care products designed to retain the properties of "virgin hair" and to prevent possible damage during the chemical and mechanical treatment. In the present application, the limitations set forth above are addressed by a personal care conditioning and/or styling composition for a keratin substrate comprising: (A) at least one conditioning and/or styling copolymer obtained by polymerizing (i) about 50 wt. % to 97 wt. % of at least one cationic or pseudo-cationic monomer; (ii) about 1 wt. % to 30 wt. % of at least one anionic monomer; and (iii) about 0.1 wt. % to 20 wt. % of at least one hydrophobic monomer; (B) at least one cosmetically acceptable excipient; and (C) optionally, at least one effective amount of personal care active ingredient.

SUMMARY OF THE INVENTION

The present application provides a personal care conditioning and/or styling composition for a keratin substrate comprising: (A) at least one conditioning and/or styling polymer obtained by polymerizing (i) about 50 wt. % to 97 wt. % of at least one cationic or pseudo-cationic monomer selected from the group consisting of diallyl dimethyl ammonium chloride (DADMAC), Hydroxyethyl-pyrrolidone-methacrylate (MO6) and/or Vinylpyrrolidone (VP); (ii) about 1 wt. % to 30 wt. % of at least one anionic monomer selected from the group consisting of (a) acrylic acid (AA), (b) acrylamido methylpropyl sulfonate (AMPS), and/or (c) sodium methyl allyl sulfonate (SMAS); and (iii) about 0.1 wt. % to 20 wt. % of at least one hydrophobic monomer selected from the group consisting of (a) polyoxyethylene (PEG)-18-behenylether-methacrylate (BEM) (b) Lauryl-ethoxylated-methacrylate (LEM), (c) stearyl acrylate (SA), (d) Streath-10-allyl-ether (BRIJ), and/or (e) vinylcaprolactam (V-Cap); (B) at least one cosmetically acceptable excipient; and (C) optionally, at least one effective amount of personal care active ingredient.

An important embodiment of the present application is to provide a personal care composition which is capable of fixing or treating hair conditioning and/or styling properties comprising detangling, wet combability, wet feel, dry combability, dry feel, sheen, static flyaway control, hydrophobicity, surface smoothening, improved deposition, no build-up, color protection, and/or curl retention. Moreover, the composition is able to provide "virgin feel condition" to the hair after multiple washes particularly with respect to (1) increased hydrophobicity, (2) improved detangling and wet combability, (3) improved deposition, and/or (4) no build-up.

According to one another aspect of the present application, the hair care composition comprising tetrapolymer is capable of providing long lasting conditioning effect even after 3 or more non-conditioning shampoo based hair washings.

Yet another aspect of the present application is to provide a method for treating or fixing regular/damaged keratin substrate comprising contacting the keratin substrate with an effective amount of personal care composition comprising a conditioning and/or styling copolymer of (i) about 50 wt. % to 97 wt. % of at least one cationic or pseudo-cationic monomer selected from the group consisting of diallyl dimethyl ammonium chloride (DADMAC), Hydroxyethyl-pyrrolidone-methacrylate (MO6) and/or Vinylpyrrolidone (VP); (ii) about 1 wt. % to 30 wt. % of at least one anionic monomer selected from the group consisting of (a) acrylic acid (AA), (b) acrylamido methylpropyl sulfonate (AMPS), and/or (c) sodium methyl allyl sulfonate (SMAS); and (iii) about 0.1 wt. % to 20 wt. % of at least one hydrophobic monomer selected from the group consisting of (a) polyoxyethylene-18-behenylether-methacrylate (BEM) (b) Lauryl-ethoxylated-methacrylate (LEM), (c) stearyl acrylate (SA), (d) Streath-10-allyl-ether (BRIJ), and/or (e) vinyl-caprolactam (V-cap); (B) at least one cosmetically acceptable excipient; and (C) optionally, at least one effective amount of personal care active ingredient; and wherein the copolymer is preferably a terpolymer or tetrapolymer having a cationic degree of substitution (Cat-DS) of greater than about 0.001 units, and wherein the cationic charge density is in the range of about 1 meq/g to about 6.5 meq/g.

Still another aspect of the present application is to provide a process for preparing a conditioning and/or styling copolymer comprising polymerizing: (i) about 50 wt. % to 97 wt. % of at least one cationic or pseudo-cationic monomer selected from the group consisting of diallyl dimethyl ammonium chloride (DADMAC), Hydroxyethyl-pyrrolidone-methacrylate (MO6) and/or Vinylpyrrolidone (VP); (ii) about 1 wt. % to 30 wt. % of at least one anionic monomer selected from the group consisting of (a) acrylic acid (AA), (b) acrylamido methylpropyl sulfonate (AMPS), and/or (c) sodium methyl allyl sulfonate (SMAS); and (iii) about 0.1 wt. % to 20 wt. % of at least one hydrophobic monomer selected from the group consisting of (a) polyoxyethylene (PEG)-18-behenylether-methacrylate (BEM) (b) Lauryl-ethoxylated-methacrylate (LEM), (c) stearyl acrylate (SA), or (d) Streath-10-allyl-ether (BRIJ), and/or (e) vinylcaprolactam (V-cap); and wherein said co-polymer is a terpolymer or tetrapolymer having a cationic degree of substitution (Cat-DS) of greater than about 0.001 units, and wherein the cationic charge density is in the range of about 1 meq/g to about 6.5 meq/g.

BRIEF DESCRIPTION OF THE FIGURES

Further embodiments of the present invention can be understood with the appended figures.

DADMAC homopolymer shampoo.

Figure 5:
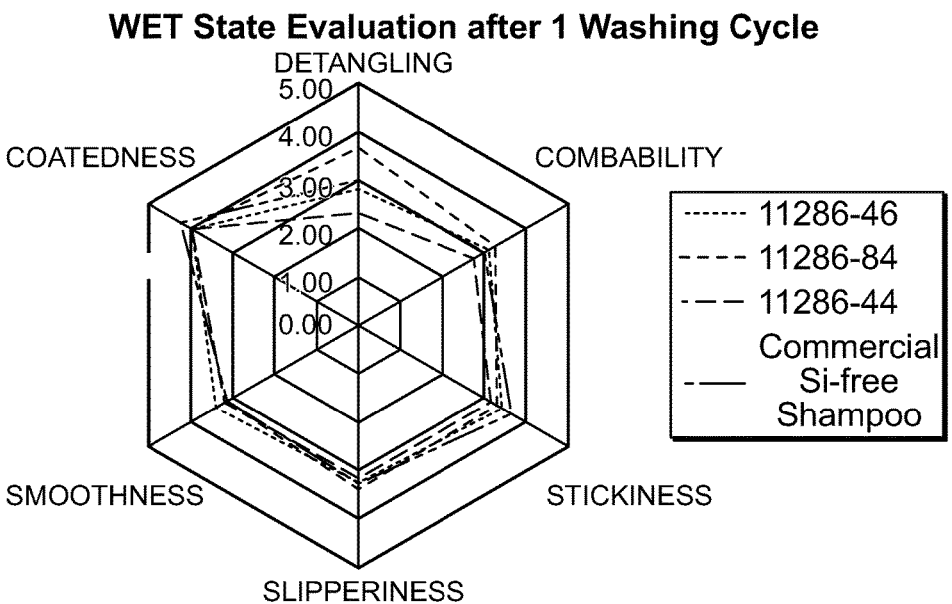

FIG. 5 shows a wet stage sensory evaluation after 1 washing cycle.

Figure 6:
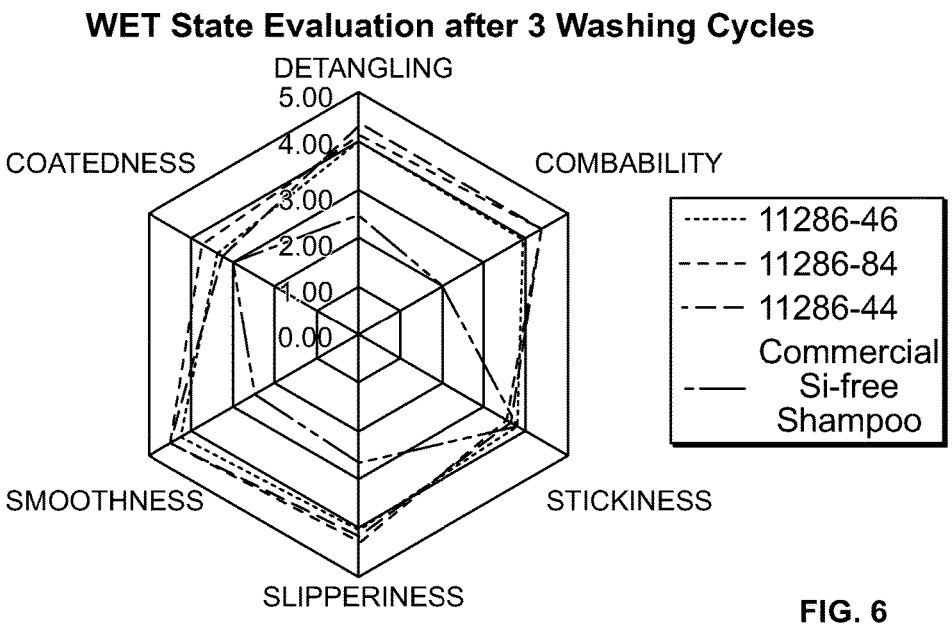

FIG. 6 shows a wet stage sensory evaluation after 3 washing cycles.

Figure 7:
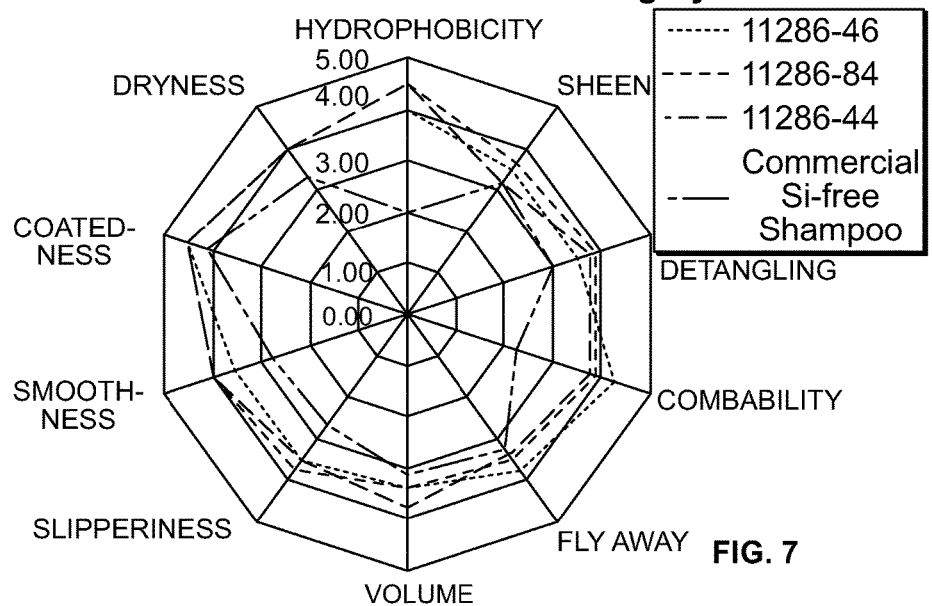

FIG. 7 shows a dry stage sensory evaluation after 1 washings cycle.

Figure 8:
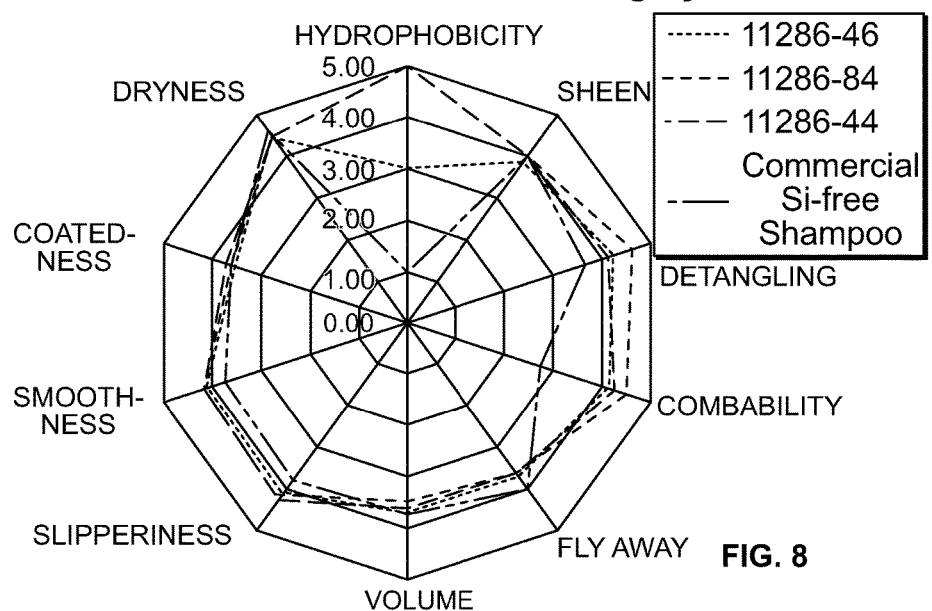

FIG. 8 shows a dry stage sensory evaluation after 3 washing cycles.

DETAILED DESCRIPTION OF THE INVENTION

While this specification concludes with claims particularly pointing out and distinctly claiming that which is regarded as the invention, it is anticipated that the invention can be more readily understood through reading the following detailed description of the invention and study of the included examples The singular forms "a," "an," and "the" include plural forms unless the context clearly dictates otherwise specified or clearly implied to the contrary by the context in which the reference is made. The term "Comprising" and "Comprises of" includes the more restrictive claims such as "Consisting essentially of" and "Consisting of".

The term "about" can indicate a difference of 10 percent of the value specified. Numerical ranges as used herein are meant to include every number and subset of numbers enclosed within that range, whether particularly disclosed or not. Further, these numerical ranges should be construed as providing support for a claim directed to any number or subset of numbers in that range.

All percentages, parts, proportions and ratios as used herein, are by weight of the total composition, unless otherwise specified. All such weights as they pertain to listed ingredients are based on the active level and, therefore; do not include solvents or by-products that may be included in commercially available materials, unless otherwise specified.

All references to singular characteristics or limitations of the present invention shall include the corresponding plural characteristic or limitation, and vice-versa, unless otherwise specified or clearly implied to the contrary by the context in which the reference is made.

As used herein, the words "preferred" or "preferably" and variants refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

References herein to "one embodiment" or "one aspect" or "one version" or "one objective" of the invention include one or more such embodiment, aspect, version or objective, unless the context clearly dictates otherwise.

All publications, articles, papers, patents, patent publications, and other references cited herein are hereby incorporated herein in their entirety for all purposes to the extent consistent with the disclosure herein.

The term "polymer" refers to a compound comprising repeating structural units (monomers) connected by covalent chemical bonds. Polymers may be further derivatized, cross-linked, grafted or end-capped. Non-limiting examples of polymers include copolymers, terpolymers, tetrapolymers, quaternary polymers, and homologues. The term "copolymer" refers to a polymer consisting essentially of two or more different types of monomers polymerized to obtain said copolymer, for example, a terpolymer or tetrapolymer and the like.

The term "conditioning agents", and grammatical variations thereof, as it relates to compositions for hair care includes cosmetically and pharmaceutically useful materials that can function as humectants, moisturizers, and emollients. It is recognized that some conditioning agents can serve more than one function in a composition, such as an emulsifying agent, a lubricant, and/or a solvent. Conditioning agents include any material which is used to give a particular conditioning benefit to hair. In hair treatment compositions, suitable conditioning agents are those which deliver one or more benefits relating to shine, softness, combability, antistatic properties, wet-handling, damage repair, manageability, detangling, body, and lubricity.

What is described herein is a personal care conditioning and/or styling composition for keratin substrate comprising: (A) at least one conditioning and/or styling co-polymer obtained by polymerizing (i) about 50 wt. % to 97 wt. % of at least one cationic or pseudo-cationic monomer selected from the group consisting of diallyl dimethyl ammonium chloride (DADMAC), Hydroxyethyl-pyrrolidone-methacrylate (MO6) and/or Vinylpyrrolidone (VP); (ii) about 1 wt. % to 30 wt. % of at least one anionic monomer selected from the group consisting of (a) acrylic acid (AA), (b) acrylamido methylpropyl sulfonate (AMPS), and/or (c) sodium methyl allyl sulfonate (SMAS); and (iii) about 0.1 wt. % to 20 wt. % of at least one hydrophobic monomer selected from the group consisting of (a) polyoxyethylene-18-behenylether-methacrylate (BEM) (b) Lauryl-ethoxylated-methacrylate (LEM), (c) stearyl acrylate (SA), (d) Streath-10-allyl-ether (BRIJ), and/or (e) vinylcaprolactam (V-Cap); (B) at least one cosmetically acceptable excipient; and (C) optionally, at least one effective amount of personal care active ingredient.

The preferred range of cationic or pseudo-cationic polymer (DADMAC/MO6/VP) for preparing a desired copolymer of present application include but not limited to 50 wt. % to 55 wt. %; 56 wt. % to 60 wt. %; 61 wt. % to 65 wt. %; 66 wt. % to 70 wt. %; 71 wt. % to 75 wt. %; 76 wt. % to 80 wt. %; 81 wt. % to 85 wt. %; 86 wt. % to 90 wt. %; 91 wt. % to 97 wt. %. Most preferred range is 86 wt. % to 97 wt. % of ter/tetra polymer.

The preferred range of an anionic monomer employed for preparing desired copolymer of present application includes but is not limited to 1 wt. % to 5 wt. %; 6 wt. % to 10 wt. %; 11 wt. % to 15 wt. %; 16 wt. % to 20 wt. %; 21 wt. % to 25 wt. %; 26 wt. % to 30 wt. %. Most preferred range is 1 wt. % to 20 wt. % of the ter/tetra polymer.

The preferred range of a hydrophobic monomer employed for preparing a desired copolymer of present application includes but is not limited to 0.01 wt. % to 5 wt. %; 6 wt. % to 10 wt. %; 11 wt. % to 15 wt. %; 16 wt. % to 20 wt. %. Most preferred range is 0.01 wt. % to 10 wt. % of the ter/tetra polymer.

The term "keratin substrate" as used herein includes skin, nails and "keratin fibers", and wherein the "keratin fibers" means hair on head, eyelashes, eyebrows and other mammalian bodily hair.

The weight average molecular weight of said copolymer of the present application, as determined by gel permeation chromatography (GPC), is at least about 10,000, preferably about 75,000 to about 2,000,000, more preferably from about 120,000 to about 500,000 g/mol, alternatively, viscometry can also be used to determine the average molecular weight of the present application.

The copolymer of use in the personal care composition of the invention has a cationic degree of substitution (Cat-DS) of greater than about 0.001 units. Preferably, the copolymer is a terpolymer or tetrapolymer having a cationic degree of substitution in the range of 0.001 to about 5.0, preferably in the range of from about 0.2 to about 3.0, more preferably in the range of about 0.4 to about 3.0.

Further, the terpolymer or tetrapolymer of the present invention has a cationic charge density in the range of from about 1 meq/g to about 8 meq/g. Preferable cationic charge density is in the range of from about 3.5 to about 7 meq/g, more preferably in the range of about 3.5 to about 6.5 meq/g.

A conditioning and/or styling terpolymer/tetrapolymer of the present application is obtained by polymerizing: (i) about 50 wt. % to 97 wt. % of at least one cationic or pseudo-cationic monomer selected from the group consisting of diallyl dimethyl ammonium chloride (DADMAC), Hydroxyethyl-pyrrolidone-methacrylate (MO6) and/or Vinylpyrrolidone (VP); (ii) about 1 wt. % to 30 wt. % of at least one anionic monomer selected from the group consisting of (a) acrylic acid (AA), (b) acrylamido methylpropyl sulfonate (AMPS), and/or (c) sodium methyl allyl sulfonate (SMAS); and (iii) about 0.1 wt. % to 20 wt. % of at least one hydrophobic monomer selected from the group consisting of (a) polyoxyethylene (PEG)-18-behenylether-methacrylate (BEM) (b) Lauryl-ethoxylated-methacrylate (LEM), (c) stearyl acrylate (SA), (d) Streath-10-allyl-ether (BRIJ), and/or (e) vinylcaprolactam (V-cap); and wherein said co-polymer is a terpolymer or tetrapolymer having a cationic degree of substitution (Cat-DS) of greater than about 0.001 units, and wherein the cationic charge density is in the range of about 1 meq/g to about 6.5 meq/g.

Non-limiting terpolymers or tetrapolymers of the present application include but are not limited to:

A. a tetrapolymer of (i) about 50 wt. % to 97 wt. % of diallyl dimethyl ammonium chloride (DADMAC); (ii) about 1 wt. % to 20 wt. % of acrylic acid (AA); (iii) about 0.1 wt. % to 20 wt. % of polyoxyethylene (PEG)-18-behenylether-methacrylate (BEM); and (iv) about 0.1 wt. % to 10 wt. % of vinylcaprolactam (V-cap); and wherein said co-polymer is a tetrapolymer having a cationic degree of substitution (Cat-DS) of greater than about 0.001 units, and wherein the cationic charge density is in the range of about 1 meq/g to about 6.5 meq/g.

B. a tetrapolymer of (i) about 50 wt. % to 97 wt. % of diallyl dimethyl ammonium chloride (DADMAC); (ii) about 1 wt. % to 20 wt. % of acrylic acid (AA); (iii) about 0.1 wt. % to 20 wt. % of Lauryl-ethoxylated-methacrylate (LEM); and (iv) about 0.1 wt. % to 10 wt. % of vinylcaprolactam (V-cap); and wherein said co-polymer is a tetrapolymer having a cationic degree of substitution (Cat-DS) of greater than about 0.001 units, and wherein the cationic charge density is in the range of about 1 meq/g to about 6.5 meq/g.

C. a tetrapoplymer of (i) about 50 wt. % to 97 wt. % of diallyl dimethyl ammonium chloride (DADMAC); (ii) about 1 wt. % to 20 wt. % of acrylic acid (AA); (iii) about 0.1 wt. % to 20 wt. % of Hydroxyethyl-pyrrolidone-methacrylate (MO6); and (iv) about 0.1 wt. % to 10 wt. % of vinylcaprolactam (V-cap); and wherein said co-polymer is a tetrapolymer having a cationic degree of substitution (Cat-DS) of greater than about 0.001 units, and wherein the cationic charge density is in the range of about 1 meq/g to about 6.5 meq/g.

D. a tetrapolymer of (i) about 50 wt. % to 97 wt. % of diallyl dimethyl ammonium chloride (DADMAC); (ii) about 1 wt. % to 20 wt. % of acrylic acid (AA); (iii) about 0.1 wt. % to 20 wt. % of Hydroxyethyl-pyrrolidone-methacrylate (MO6); and (iv) about 0.1 wt. % to 10 wt. % of Lauryl-ethoxylated-methacrylate (LEM); and wherein said co-polymer is a tetrapolymer having a cationic degree of substitution (Cat-DS) of greater than about 0.001 units, and wherein the cationic charge density is in the range of about 1 meq/g to about 6.5 meq/g.

E. a terpolymer of (i) about 50 wt. % to 97 wt. % of diallyl dimethyl ammonium chloride (DADMAC), a cationic monomer; (ii) about 1 wt. %-30 wt. % of acrylamido methylpropyl sulfonate (AMPS), an anionic monomer; and (iii) about 0.1 wt. % to 20 wt. % stearyl acrylate (SA), a hydrophobic monomer; and wherein said co-polymer is a tetrapolymer having a cationic degree of substitution (Cat-DS) of greater than about 0.001 units, and wherein the cationic charge density is in the range of about 1 meq/g to about 6.5 meq/g.

F. a terpolymer of (i) about 50 wt. % to 97 wt. % of diallyl dimethyl ammonium chloride (DADMAC), a cationic monomer; (ii) about 1 wt. % to 30 wt. % of sodium methyl allyl sulfonate (SMAS), an anionic monomer; and (iii) about 0.1 wt. % to 20 wt. % polyoxyethylene (PEG)-18-behenylether methacrylate (BEM), a hydrophobic monomer; and wherein said co-polymer is a tetrapolymer having a cationic degree of substitution (Cat-DS) of greater than about 0.001 units, and wherein the cationic charge density is in the range of about 1 meq/g to about 6.5 meq/g.

G. a terpolymer of (i) about 50 wt. % to 97 wt. % of diallyl dimethyl ammonium chloride (DADMAC), a cationic monomer; (ii) about 1 wt. % to 30 wt. % of sodium methyl allyl sulfonate (SMAS), an anionic monomer; and (iii) about 0.1 wt. % to 20 wt. % stearyl acrylate (SA), a hydrophobic monomer; and wherein said co-polymer is a tetrapolymer having a cationic degree of substitution (Cat-DS) of greater than about 0.001 units, and wherein the cationic charge density is in the range of about 1 meq/g to about 6.5 meq/g.

H. a terpolymer of (i) about 50 wt. % to 97 wt. % of diallyl dimethyl ammonium chloride (DADMAC), a cationic monomer; (ii) about 1 wt. % to 30 wt. % of acrylic acid (AA), an anionic monomer; and (iii) about 0.1 wt. % to 20 wt. % polyoxyethylene (PEG)-18-behenylether methacrylate (BEM), a hydrophobic monomer; and wherein said co-polymer is a tetrapolymer having a cationic degree of substitution (Cat-DS) of greater than about 0.001 units, and wherein the cationic charge density is in the range of about 1 meq/g to about 6.5 meq/g.

I. a tetrapolymer of (i) about 50 wt. % to 97 wt. % of diallyl dimethyl ammonium chloride (DADMAC), a cationic monomer; (ii) about 1 wt. % to 30 wt. % of acrylic acid (AA), an anionic monomer; (iii) about 0.1 wt. % to 20 wt. % polyoxyethylene (PEG)-18-behenylether methacrylate (BEM), a hydrophobic monomer; and (iv) about 0.1 wt. % to 20 wt. % vinylcaprolactam (V-cap), a hydrophobic monomer; and wherein said co-polymer is a tetrapolymer having a cationic degree of substitution (Cat-DS) of greater than about 0.001 units, and wherein the cationic charge density is in the range of about 1 meq/g to about 6.5 meq/g.

J. a tetrapolymer of (i) about 50 wt. % to 97 wt. % of diallyl dimethyl ammonium chloride (DADMAC), a cationic monomer; (ii) about 50 wt. % to 97 wt. % of Vinylpyrrolidone (VP), a pseudo-cationic monomer; (iii) about 1 wt. % to 30 wt. % of acrylic acid (AA), an anionic monomer; and (iv) about 0.1 wt. % to 20 wt. % polyoxyethylene (PEG)-18-behenylether methacrylate (BEM), a hydrophobic monomer; and wherein said co-polymer is a tetrapolymer having a cationic degree of substitution (Cat-DS) of greater than about 0.001 units, and wherein the cationic charge density is in the range of about 1 meq/g to about 6.5 meq/g.

A process for preparing a conditioning and/or styling copolymer comprising polymerizing: (i) about 50 wt. % to 97 wt. % of at least one cationic or pseudo-cationic monomer selected from the group consisting of diallyl dimethyl ammonium chloride (DADMAC) and/or Vinylpyrrolidone (VP); (ii) about 1 wt. % to 30 wt. % of at least one anionic monomer selected from the group consisting of (a) acrylic acid (AA), (b) acrylamido methylpropyl sulfonate (AMPS), and/or (c) sodium methyl allyl sulfonate (SMAS); and (iii)

about 0.1 wt. % to 20 wt. % of at least one hydrophobic monomer selected from the group consisting of (a) polyoxyethylene (PEG)-18-behenylether-methacrylate (BEM) (b) Lauryl-ethoxylated-methacrylate (LEM), (c) stearyl acrylate (SA), (d) Streath-10-allyl-ether (BRIJ), or (e) vinyl-caprolactam (V-cap), and/or (f) Hydroxyethyl-pyrrolidone-methacrylate (MO6); and wherein said co-polymer is a terpolymer or tetrapolymer having a cationic degree of substitution (Cat-DS) of greater than about 0.001 units, and wherein the cationic charge density is in the range of about 1 meq/g to about 6.5 meq/g.

According to one important aspect of the present application, the above disclosed terpolymers and tetrapolymers of the present application can advantageously be combined and formulated with (1) at least one anionic, cationic, nonionic and/or zwitter-ionic/amphoteric polymers or mixtures thereof, (2) at least one personal care active ingredient, and/or (3) at least one cosmetically acceptable excipient.

The cationic polymers that can be used along with conditioning and/or styling copolymer of this application are those known to improve the cosmetic properties of hair which may be normal or damaged in nature. The expression "cationic polymer" as used herein, indicates any polymer containing cationic groups and/or ionizable groups in cationic groups. The cationic polymers used generally have a molecular weight the average number of which falls between about 500 and 5,000,000 and preferably between 1000 and 3,000,000. The preferred cationic polymers are chosen from among those containing units including primary, secondary, tertiary, and/or quaternary amine groups that may either form part of the main polymer chain or a side chain. Useful cationic polymers include known polyamine, polyaminoamide, and quaternary polyammonium types of polymers, such as:

(1) Homopolymers and copolymers derived from acrylic or methacrylic esters or amides. The copolymers can contain one or more units derived from acrylamides, methacrylamides, diacetone acrylamides, acrylamides and methacrylamides, acrylic or methacrylic acids or their esters, vinyllactams such as vinyl pyrrolidone or vinyl caprolactam, and vinyl esters. Specific examples include: copolymers of acrylamide and dimethyl amino ethyl methacrylate quaternized with dimethyl sulfate or with an alkyl halide; copolymers of acrylamide and methacryloyl oxyethyl trimethyl ammonium chloride; the copolymer of acrylamide and methacryloyl oxyethyl trimethyl ammonium methosulfate; copolymers of vinyl pyrrolidone/dialkylaminoalkyl acrylate or methacrylate, optionally quaternized, such as the products sold under the name GAFQUAT by Ashland; the dimethyl amino ethyl methacrylate/vinyl caprolactam/vinyl pyrrolidone terpolymers, such as the product sold under the name GAFFIX VC 713 by Ashland; the vinyl pyrrolidone/methacrylamidopropyl dimethylamine copolymer, marketed under the name STYLEZE CC 10 by Ashland; the vinyl pyrrolidone/quaternized dimethyl amino propyl methacrylamide copolymers such as the product sold under the name GAFQUAT HS 100 by Ashland; and the vinyl pyrrolidone/dimethylaminopropyl methacrylamide/$C_9$-$C_{24}$ alkyldimethylaminopropyl methacrylic acid quaternized terpolymers described in U.S. Pat. No. 6,207,778 and marketed under the name STYLEZE-W20 by Ashland.

(2) Derivatives of cellulose ethers containing quaternary ammonium groups, such as hydroxy ethyl cellulose quaternary ammonium that has reacted with an epoxide substituted by a trimethyl ammonium group.

(3) Derivatives of cationic cellulose such as cellulose copolymers or derivatives of cellulose grafted with a hydrosoluble quaternary ammonium monomer, as described in U.S. Pat. No. 4,131,576, such as the hydroxy alkyl cellulose, and the hydroxymethyl-, hydroxyethyl- or hydroxypropyl-cellulose grafted with a salt of methacryloyl ethyl trimethyl ammonium, methacrylamidopropyl trimethyl ammonium, or dimethyl diallyl ammonium.

(4) Cationic polysaccharides such as described in U.S. Pat. Nos. 3,589,578 and 4,031,307, guar gums containing cationic trialkyl ammonium groups, guar gums modified by a salt, e.g., chloride of 2,3-epoxy propyl trimethyl ammonium, Cassia, Chitosan, Chitin and the like.

(5) Polymers composed of piperazinyl units and alkylene or hydroxy alkylene divalent radicals with straight or branched chains, possibly interrupted by atoms of oxygen, sulfur, nitrogen, or by aromatic or heterocyclic cycles, as well as the products of the oxidation and/or quaternization of such polymers.

(6) Water-soluble polyamino amides prepared by polycondensation of an acid compound with a polyamine. These polyamino amides may be reticulated.

(7) Derivatives of polyamino amides resulting from the condensation of polyalcoylene polyamines with polycarboxylic acids followed by alcoylation by bi-functional agents.

(8) Polymers obtained by reaction of a polyalkylene polyamine containing two primary amine groups and at least one secondary amine group with a dioxycarboxylic acid chosen from among diglycolic acid and saturated dicarboxylic aliphatic acids having 3 to 8 atoms of carbon. Such polymers are described in U.S. Pat. Nos. 3,227,615 and 2,961,347.

(9) The cyclopolymers of alkyl dialyl amine or dialkyl diallyl ammonium such as the homopolymer of dimethyl diallyl ammonium chloride and copolymers of diallyl dimethyl ammonium chloride and acrylamide.

(10) Quaternary diammonium polymers such as hexadimethrine chloride. Polymers of this type are described particularly in U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945, and 4,027,020.

(11) Quaternary polyammonium polymers, including, for example, Mirapol® A 15, Mirapol® AD1, Mirapol® AZ1, and Mirapol® 175 products sold by Miranol.

(12) The quaternary polymers of vinyl pyrrolidone and vinyl imidazole such as the products sold under the names Luviquat® FC 905, FC550, and FC 370 by BASF.

(13) Quaternary polyamines.

(14) Reticulated polymers known in the art.

Suitable Polyquaternium type of cationic polymers for the present application would include but not limited to Polyquaternium 4, Polyquaternium 5, Polyquaternium 6, Polyquaternium 7, Polyquaternium 10, Polyquaternium 11, Polyquaternium 15, Polyquaternium 16, Polyquaternium 22, Polyquaternium 28, Polyquaternium 32, Polyquaternium 37, Polyquaternium 39, Polyquaternium 46, Polyquaternium 47, Polyquaternium 53, Polyquaternium 55, Polyquaternium 67, and/or Polyquaternium 87. Other polymers known by their CTFA category name "Quaternium" are suitable for the present application would include but not limited to Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-81, Quaternium-82, Quaternium-83 and Quaternium-84.

Other cationic polymers that may be used within the context of the invention are cationic proteins or hydrolyzed cationic proteins, polyalkyleneimines such as polyethyleneimines, polymers containing vinyl pyridine or vinyl pyridinium units, condensates of polyamines and epichlorhydrins, quaternary polyurethanes, and derivatives of chitin.

The anionic polymers that can be employed along with a conditioning and/or styling copolymer of this application would include but are not limited to carboxylic acids such as acrylic acid (AA), methacrylic acid (MAA), 2-acrylamido-2-methylpropanesulfonic acid (AMPS), crotonic acid, styrene sulfonic acid, itconic acid, and the like.

Preferred anionic homo and copolymer of the present application would include but are not limited to (a) Homo- or copolymers of acrylic or methacrylic acid or salts thereof; (b) Copolymers of acrylic or methacrylic acids with a mono-ethylenic monomer such as ethylene, styrene, vinyl esters, acrylic acid esters or methacrylic acid esters. These copolymers can be grafted onto a polyalkylene glycol and optionally crosslinked; (c) Copolymers comprising: (i) one or more maleic, fumaric or itaconic acids or anhydrides and (ii) at least one monomer selected from vinyl esters, vinyl ethers, vinyl halides, phenylvinyl derivatives, acrylic acid and its esters, the anhydride functions of these copolymers optionally being monoesterified or monoamidated; (d) Copolymers comprising: (i) one or more maleic, citraconic or itaconic anhydrides and (ii) one or more monomers selected from allylic or methallylic esters optionally containing one or more acrylamide, methacrylamide, alpha-olefin, acrylic or methacrylic ester, acrylic or methacrylic acid or vinylpyrrolidone groups in their chain, the anhydride functions of these copolymers optionally being monoesterified or monoamidated; (e) Polyacrylamides containing carboxylate groups; (f) The polymers comprising sulphonic groups are polymers containing vinylsulphonic, styrenesulphonic, naphthalenesulphonic or acrylamidoalkylsulphonic units.

Other preferred anionic copolymers are selected from the group consisting of but not limited to vinyl acetate/crotonic acid copolymer, vinyl acetate/acrylate copolymer, vinyl acetate/vinyl neodecanoate/crotonic acid copolymer, sodium acrylate/vinyl alcohol copolymer, sodium polystyrene sulphate, ethyl acrylate/N-tert-Butyl acrylamide/acrylic acid copolymer, vinylpyrrolidone/vinyl acetate/itaconic acid copolymer, acrylic acid/acrylamide copolymer and sodium salts thereof, homo and copolymers of acrylic acid and/or methacrylic acid and/or salts thereof, acrylate/hydroxyacrylate copolymer, octylacrylamide/acrylate copolymer, octylacrylamide/methacrylic ester copolymer, butyl acrylate/N-vinylpyrrolidone copolymer, methyl vinyl ether/maleic acid copolymer and the ethyl, isopropyl and butyl esters, silicone/acrylic acid or methacrylic acid copolymer, polyurethanes based on diisocyanates with terminal acid groups.

The amphoteric polymers cab be selected from the following polymers: (1) Polymers resulting from the copolymerization of a monomer derived from a vinyl compound bearing a carboxylic group such as, more particularly, acrylic acid, methacrylic acid, maleic acid, alpha-chloroacrylic acid, and a basic monomer derived from a substituted vinyl compound containing at least one basic atom, such as, more particularly, dialkylaminoalkyl methacrylate and acrylate, dialkylaminoalkylmethacrylamides and acrylamides. (2) Polymers containing units derived from: a) at least one monomer selected from acrylamides and methacrylamides substituted on the nitrogen with an alkyl radical, b) at least one acidic comonomer containing one or more reactive carboxylic groups, and c) at least one basic comonomer such as esters containing primary, secondary, tertiary and quaternary amine substituents of acrylic and methacrylic acids and the product of quaternization of dimethylaminoethyl methacrylate with dimethyl or diethyl sulphate.

Further, the exemplary amphoteric polymer can selected from the group N-Octylacrylamid/Acrylsäure/tertiary-Butylaminoethylmethacrylat-Copolymer, N-Octylacrylamld/Methacrylsaure/tertiary-butylaminoethylmethacrylat-Copolymer group and copolymers of Methacryloylbetain/alkyl methacrylates, copolymers of monomers having carboxyl— and/or sulfonic groups, particularly acrylic acid, methacrylic acid, itaconic acid, and monomers containing amino groups, especially Monoalkylaminoalkylacrylate, dialkylaminoalkyl, Mono alkylamino alkylmethacrylate, dialkylaminoalkyl, Mono-alkylaminoalkylacrylamide, dialkylaminoalkylacrylamides, Mono-alkylaminoalkylmethacrylamide, Dialkylaminoalkylmethacrylamide, and copolymers of N-octyl acrylamide, methyl methacrylate, hydroxypropyl methacrylate.

Nonionic polymers having at least one fatty chain and at least one hydrophilic unit, are preferably chosen from: (1) celluloses modified with groups containing at least one fatty chain such as, for example: hydroxyethyl celluloses modified with groups containing at least one fatty chain such as alkyl, arylalkyl or alkylaryl groups or mixtures thereof, and in which the alkyl groups are preferably $C_8$-$C_{22}$; (2) hydroxypropyl guars modified with groups containing at least one fatty chain; (3) polyether urethanes containing at least one fatty chain such as a $C_8$-$C_{30}$ alkyl or alkenyl group; (4) copolymers of $C_1$-$C_6$ alkyl methacrylates or acrylates and of amphiphilic monomers comprising at least one fatty chain; (5) copolymers of hydrophilic methacrylates or acrylates and of hydrophobic monomers comprising at least one fatty chain; (6) polyurethane polyethers comprising in their chain both hydrophilic blocks usually of polyoxyethylenated nature and hydrophobic blocks which may be aliphatic sequences alone and/or cycloaliphatic and/or aromatic sequences; and (7) polymers with an aminoplast ether backbone containing at least one fatty chain. Other relevant nonionic polymers which are disclosed in US Patent Application No's. 20070134191 and 20110165108 may be employed for the purposes of the present application.

The polymerization of the polymer useful herein is carried out by any appropriate method known in the prior art by a person skilled in the art. Particularly, the polymerization is carried out by any one of the methods disclosed in "*Principles of Polymerization*" $4^{th}$ edition, 2004, Wiley by George Odian and is referred and disclosed herein in its entirety. Further, the polymerization of terpolymer or tetrapolymer of the present application may contain a suitable catalyst or initiators such as amines, bases, organic acids and/or photo-initiators. However, the preferred polymerization technique employed to prepare a conditioning polymer would include but not limited to radical polymerization, emulsion polymerization, ionic chain polymerization, bulk polymerization, suspension polymerization or precipitation polymerization.

It is contemplated to employ at least one personal care active ingredient for preparing a personal care composition of the present application comprising a conditioner terpolymer or tetrapolymer and at least one cosmetically acceptable agent, wherein, the preferred personal care active ingredient of the present application would include but not limited to Carnitine, Betain Aminoacids as i.e. valine, glycine, arginine, allantoin, tocopherol nicotinate, niacinamide, retinyl propionate, palmitoyl-gly-his-lys, phytosterol, polyphenolic compounds, flavonoids, flavones, flavonols, isoflavone, dexpanthenol, panthenol, bisabolol, farnesol, phytantriol, salicylic acid, zinc/sodium pyridinethione salts, piroctone olamine, selenium disulfide, tetrahydrocurcumin, glucosamine, N-acteyl glucosamine, vitamin B3, retinoids, peptides, phytosterol, dialkanoyl hydroxyproline, hexamidine, salicylic acid, N-acyl amino acids, escolols, sunscreen actives, UV-A/UV-B protecting agent, UV filters, water soluble vitamins, oil soluble vitamins, hesperedin, mustard seed extract, glycyrrhizic acid, glycyrrhetinic acid, carnosine, Butylated Hydroxytoluene (BHT) and Butylated Hydroxyanisole (BHA), ergothioneine, vanillin, vanillin derivatives, diethylhexyl syrinylidene malonate, melanostatine, sterol esters, fatty acids, poly-unsaturated fatty acids, anti-fungal agents, thiol compounds, N-acetyl cysteine, glutathione, thioglycolate, β-carotene, ubiquinone, amino acids, idebenone, dehydroacetic acid, Licohalcone A, creatine, creatinine, feverfew extract, yeast extract, beta glucans, alpha glucans, alone or in combination.

The preferred polyphenolic compounds include flavonoids such as those broadly disclosed in U.S. Pat. No. 5,686,082. Exemplary flavonoids include at least one flavones, flavanols, isoflavones, coumarins, chromones, dicoumarols, chromanones, chromanols, and/or isomers (e.g., cis/trans isomers). Suitable flavones and isoflavones include unsubstituted flavone, unsubstituted isoflavone, daidzein (7,4'-dihydroxy isoflavone), genistein (5,7,4'-trihydroxy isoflavone), equol (7,4'-isoflavandiol), 5,7-dihydroxy-4'-methoxy isoflavone, 7,2'-dihydroxy flavone, 3',4'-dihydroxy naphthoflavone, 7,8-benzoflavone, 4'-hydroxy flavone, 5,6-benzoflavone, soy isoflavones (e.g., isoflavones extracted from soy) and other plant sources of such mixtures (e.g., red clover), and mixtures thereof. Other suitable flavonoids include hesperitin, hesperidin, quercetin and mixtures thereof. Other polyphenolic compounds include tetrahydrocurcuminoids. Tetrahydrocurcuminoids include tetrahydrocurcumin, tetrahydrodemethoxycurcumin, and tetrahydrobismethoxycurcumin.

The effective amount of personal care active ingredient employed in the present application is in the range of from about 0.01 wt. % to about 10 wt. %, preferably about 0.1 wt. % to about 5.0 wt. % and more preferably in the range of 0.05 wt. % to about 3.0 wt. % of the total composition.

The personal care composition of present application is capable of fixing or treating hair and features conditioning and/or styling properties such as detangling, wet combability, wet feel, dry combability, dry feel, sheen, static flyaway control, hydrophobicity, surface smoothening, improved deposition, no build-up, color protection, and/or curl retention. Further, the personal care composition comprising a terpolymer or tetrapolymer of present application is able to provide "virgin feel condition" to the hair after multiple washes.

The personal care composition of present application can be an appropriate product selected from the group consisting of hair-care products, shampoos, hair conditioners, 2 in 1 shampoos, leave in and rinse off conditioners, hair treatments including intensive treatments, styling and treating hair compositions, hair perming products, hair straightners, hair relaxants, hair sprays and lacquers, permanent hair dyeing systems, hair styling mousses, hair gels, semi-permanent hair dyeing systems, temporary hair dyeing systems, hair bleaching agents, permanent hair wave systems, hair setting formulations, non-coloring hair preparations, hair-frizz-control gels, hair leave-in conditioners, hair pomades, hair de-tangling products, hair fixatives, hair conditioning mists, hair care pump sprays and other non-aerosol sprays, skin-care products, hair cuticle coats, skin care moisturizing mists, skin wipes, pore skin wipes, pore cleaners, blemish reducers, skin exfoliators, skin desquamation enhancers, skin towelettes, skin protection ointments, skin powders, skin pads, paste masks and muds, face masks, facial cleansing products, anti-acne preparations, bath products, shower products, liquid soaps, bar soaps, body oils, body lotions, body gels, body and hand preparations, face and body washes, bath salts, bath and body milks, foam baths, synthetic and non-synthetic soap bars, hand liquids, shaving lotions, shaving and aftershave preparations, pre-shaves and pre-electric shaves, nail varnishes, nail polish, nail polish remover, nail creams and lotions, cuticle softeners, nail conditioners, eye shadows, mascaras, eye liners, eye shadows, blushes, makeup, eye shadow sticks, baby lotions, baby baths and shampoos, baby conditioners, fragrances and/or odoriferous ingredients consisting preparations, dentifrices, deodorizing and antiperspirant preparations, decorative preparations, light protection formulations, treatment creams, lipsticks, dry and moist make-up, rouge, powders, depilatory agents, sun care products, compositions comprising UV blockers or UV protectors, anti-aging products, foundations, face powders, moisturizing preparations, tanning preparations, nose strips, make-up removers, cold creams, mousses, shower gels, personal care rinse-off products, gels, scrubbing cleansers, astringents, lip balms, lip glosses, anhydrous creams and lotions, oil/water, water/oil, multiple and macro and micro emulsions, water-resistant creams and lotions, mouth-washes, massage oils, toothpastes, clear gels and sticks, ointment bases, topical wound-healing products, aerosol talc, barrier sprays, vitamin, herbal-extract preparations, and/or controlled-release personal care products.

The personal care composition of present invention can be formulated in several required forms according to their necessity, and the non-limiting forms include emulsion, lotion, gel, vesicle dispersion, paste, cream, solid stick, mousse, shampoo, spray, balm, wipe, milk, foam, jellies, liquid, tonics, and/or enamel.

As used herein, the term "cosmetically acceptable excipient" means any ingredient/compound or mixture of ingredients/compounds or compositions that are typically employed to produce other desirable effects in personal care compositions. The preferred cosmetically acceptable excipients include but not limited to preservatives, antioxidants, chelating agents, sunscreen agents, proteins, amino acids, vitamins, dyes, hair coloring agents, plant extracts, plant derivatives, plant tissue extracts, plant seed extracts, plant oils, botanicals, botanical extracts, humectants, fragrances, perfumes, oils, emollients, lubricants, butters, penetrants, thickeners, viscosity modifiers, thickeners, polymers, resins, hair fixatives, film formers, surfactants, detergents, emulsifiers, opacifying agents, volatiles, propellants, liquid vehicles, carriers, salts, pH adjusting agents, neutralizing agents, buffers, hair conditioning agents, anti-static agents, anti-frizz agents, anti-dandruff agents, hair waving agents, hair straightening agents, relaxers, absorbents, fatty substances, gelling agents, moisturizers, hydrophilic or lipophilic active agent, preserving agents, fillers, dyestuffs, reducing agents, cosmetic oils, perfumes, liquid vehicles, solvents, carriers, silicones, and combinations thereof.

Suitable rheology modifiers and thickeners include synthetic and semi-synthetic rheology modifiers. Exemplary synthetic rheology modifiers include acrylic based polymers and copolymers. One class of acrylic based rheology modifiers are the carboxyl functional alkali-swellable and alkali-soluble thickeners (ASTs) produced by the free-radical polymerization of acrylic acid alone or in combination with other ethylenically unsaturated monomers. The polymers can be synthesized by solvent/precipitation as well as emulsion polymerization techniques. Exemplary synthetic rheology modifiers of this class include homopolymers of acrylic acid or methacrylic acid and copolymers polymerized from one or more monomers of acrylic acid, substituted acrylic acid, and salts and $C_1$-$C_{30}$ alkyl esters of acrylic acid and substituted acrylic acid. As defined herein, the substituted acrylic acid contains a substituent positioned on the alpha and/or beta carbon atom of the molecule wherein the substituent is preferably and independently selected from $C_{1-4}$ alkyl, —CN, and —COOH. Optionally, other ethylenically unsaturated monomers such as, for example, styrene, vinyl acetate, ethylene, butadiene, acrylonitrile, as well as mixtures thereof can be copolymerized into the backbone. The foregoing polymers are optionally crosslinked by a monomer that contains two or more moieties that contain ethylenic unsaturation. In one aspect, the crosslinker is selected from a polyalkenyl polyether of a polyhydric alcohol containing at least two alkenyl ether groups per molecule. Other Exemplary crosslinkers are selected from allyl ethers of sucrose and allyl ethers of pentaerythritol, and mixtures thereof. These polymers are more fully described in U.S. Pat. Nos. 5,087,445; 4,509,949; and 2,798,053 herein incorporated by reference in its entirety.

Commercially available Carbomers include Carbopol® polymers 934, 940, 941, 956, 980 and 996 available from Lubrizol Advanced Materials, Inc. In another embodiment the AST rheology modifier is selected from a crosslinked copolymer polymerized from a first monomer selected from one or more monomers of (meth) acrylic acid, substituted acrylic acid, and salts of (meth)acrylic acid and substituted acrylic acid and a second monomer selected from one or more $C_1$-$C_5$ alkyl acrylate esters of (meth)acrylic acid. These polymers are designated under the INCI name of Acrylates Copolymer. Acrylates Copolymers are commercially available under the trade names Aculyn® 33 from Rohm and Haas and Carbopol® Aqua SF-1 from Lubrizol Advanced Materials, Inc and Surfathix N from Ashland. In a further aspect the rheology modifier is selected from a crosslinked copolymer polymerized from a first monomer selected from one or more monomers of acrylic acid, substituted acrylic acid, salts of acrylic acid and salts of substituted acrylic acid and a second monomer selected from one or more $C_{10}$-$C_{30}$ alkyl acrylate esters of acrylic acid or methacrylic acid. In one aspect, the monomers can be polymerized in the presence of a steric stabilizer such as disclosed in U.S. Pat. No. 5,288,814 which is herein incorporated by reference. Some of the forgoing polymers are designated under INCI nomenclature as Acrylates/C10-30 Alkyl Acrylate Crosspolymer and are commercially available under the trade names Carbopol® 1342 and 1382, Carbopol® Ultrez 20 and 21, Carbopol® ETD 2020 and Pemulen® TR-1 and TR-2 from Lubrizol Advanced Materials, Inc. Any vinyl or acrylic based rheology modifiers are suitable. Acrylates/Ceteth-20 itaconate Copolymer available as 2001 from Akzo, Acrylate beheneth-25 Methacrylate Copolymer commercially available as Aculyn 28 from Rohm and Haas (now DOW Chemical), Aminoaryloyl Dimethyltaurate/VP Copolymer available as Aristoflex AVC from Clariant.

Another class of synthetic rheology modifiers and thickeners suitable for use in accordance with an embodiment of the present invention includes hydrophobically modified ASTs commonly referred to as hydrophobically modified alkali-swellable and alkali-soluble emulsion (HASE) polymers. Typical HASE polymers are free radical addition polymers polymerized from pH sensitive or hydrophilic monomers (e.g., acrylic acid and/or methacrylic acid), hydrophobic monomers (e.g., $C_1$-$C_{30}$ alkyl esters of acrylic acid and/or methacrylic acid, acrylonitrile, styrene), an "associative monomer", and an optional crosslinking monomer. The associative monomer comprises an ethylenically unsaturated polymerizable end group, a non-ionic hydrophilic midsection that is terminated by a hydrophobic end group. The non-ionic hydrophilic midsection comprises a polyoxyalkylene group, e.g., polyethylene oxide, polypropylene oxide, or mixtures of polyethylene oxide/polypropylene oxide segments. The terminal hydrophobic end group is typically a $C_8$-$C_{40}$ aliphatic moiety. Exemplary aliphatic moieties are selected from linear and branched alkyl substituents, linear and branched alkenyl substituents, carbocyclic substituents, aryl substituents, aralkyl substituents, arylalkyl substituents, and alkylaryl substituents. In one aspect, associative monomers can be prepared by the condensation (e.g., esterification or etherification) of a polyethoxylated and/or polypropoxylated aliphatic alcohol (typically containing a branched or unbranched $C_8$-$C_{40}$ aliphatic moiety) with an ethylenically unsaturated monomer containing a carboxylic acid group (e.g., acrylic acid, methacrylic acid), an unsaturated cyclic anhydride monomer (e.g., maleic anhydride, itaconic anhydride, citraconic anhydride), a monoethylenically unsaturated monoisocyanate (e.g., α,α-dimethyl-m-isopropenyl benzyl isocyanate) or an ethylenically unsaturated monomer containing a hydroxyl group (e.g., vinyl alcohol, allyl alcohol). Polyethoxylated and/or polypropoxylated aliphatic alcohols are ethylene oxide and/or propylene oxide adducts of a monoalcohol containing the $C_8$-$C_{40}$ aliphatic moiety. Non-limiting examples of alcohols containing a $C_8$-$C_{40}$ aliphatic moiety are capryl alcohol, iso-octyl alcohol (2-ethyl hexanol), pelargonic alcohol (1-nonanol), decyl alcohol, lauryl alcohol, myristyl alcohol, cetyl alcohol, cetyl alcohol, cetearyl alcohol (mixture of $C_{16}$-$C_{18}$ monoalcohols), stearyl alcohol, isostearyl alcohol, elaidyl alcohol, oleyl alcohol, arachidyl alcohol, behenyl alcohol, lignoceryl alcohol, ceryl alcohol, montanyl alcohol, melissyl, lacceryl alcohol, geddyl alcohol, and $C_2$-$C_{20}$ alkyl substituted phenols (e.g., nonyl phenol), and the like.

Exemplary HASE polymers are disclosed in U.S. Pat. Nos. 3,657,175; 4,384,096; 4,464,524; 4,801,671; and 5,292,843, which are herein incorporated by reference. In addition, an extensive review of HASE polymers is found in Gregory D. Shay, Chapter 25, "Alkali-Swellable and Alkali-Soluble Thickener Technology A Review", Polymers in Aqueous Media—Performance Through Association, Advances in Chemistry Series 223, J. Edward Glass (ed.), ACS, pp. 457-494, Division Polymeric Materials, Washington, D.C. (1989), the relevant disclosures of which are incorporated herein by reference. The HASE polymers are commercially available from Rohm & Haas under the trade designations Aculyn® 22 (INCI Name: Acrylates/Steareth-20 Methacrylate Copolymer), Aculyn® 44 (INCI Name: PEG-150/Decyl Alcohol/SMDI Copolymer), Aculyn 46® (INCI Name: PEG-150/Stearyl Alcohol/SMDI Copolymer), and Aculyn® 88 (INCI Name: Acrylates/Steareth-20 Methacrylate Crosspolymer).

Another class of synthetic and semi-synthetic rheology modifiers and thickeners suitable for use in accordance with an embodiment of the present invention includes cationically modified acrylic polymers and copolymers and cationically modified cellulose ethers. The acrylic polymers and copolymers and cellulose ethers are cationically modified via quaternization. For the acrylic polymers and copolymers, quaternization can occur by polymerizing a quaternized monomer into the acrylic polymer backbone or by post functionalizing the acrylic polymer with a quaternizing agent. An exemplary quaternary acrylic polymer is designated under INCI nomenclature as Polyquaternium-37 and is commercially available under the trade names Synthalen CR21 and Synthalen CN, from 3V Inc. The quaternized celluloses are prepared by post functionalizing the desired cellulosic backbone (e.g., hydroxyethyl cellulose) with a quaternizing agent such as a quaternary ammonium salt (e.g., diallyldimethyl ammonium chloride, trimethyl ammonium chloride substituted epoxide). Exemplary quaternary cellulosic polymers are designated under the INCI names Polyquaternium-4, Polyquaternium-10, and Polyquaternium-67.

Other rheology modifiers suitable for use in the personal care compositions of the invention are disclosed in U.S. Pat. No. 7,205,271 the disclosure of which is herein incorporated by reference.

Suitable surfactants or surfactant systems for preparing a personal care composition comprising a conditioning and/or styling copolymer of the present application can be selected from anionic, non-ionic, amphoteric, cationic and mixtures thereof. The contemplated surfactants for use herein are as follows:

(A) Anionic Surfactants: Anionic surfactants are particularly useful in accordance with certain embodiments of the present application. Surfactants of the anionic type that may be useful include:

(1) Sulfonates and Sulfates: Suitable anionic surfactants include sulfonates and sulfates such as alkyl sulfates, alkylether sulfates, alkyl sulfonates, alkylether sulfonates, alkylbenzene sufonates, alkylbenzene ether sulfates, alkylsulfoacetates, secondary alkane sulfonates, secondary alkylsulfates, alkyl sulfosuccinates and the like. Further, examples of anionic surfactants include water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like.

(2) Phosphates and Phosponates: Suitable anionic surfactants also include phosphates such as alkyl phosphates, alkylether phosphates, aralkylphosphates, and aralkylether phosphates. Examples include a mixture of mono-, di- and tri-(alkyltetraglycolether)-o-phosphoric acid esters generally referred to as trilaureth-4-phosphate commercially available under the trade designation HOSTAPHAT 340KL from Clamant Corp., as well as PPG-5 ceteth 10 phosphate available under the trade designation CRODAPHOS SG from Croda Inc., Parsipanny, N.J.

(3) Amine Oxides: Suitable anionic surfactants also include amine oxides. Examples of amine oxide surfactants include lauryldimethylamine oxide, laurylamidopropyldimethylamine oxide, and/or cetyl amine oxide.

(B) Amphoteric Surfactants: Surfactants of the amphoteric type include surfactants having tertiary amine groups which may be protonated as well as quaternary amine containing zwitterionic surfactants. Those that may be useful include:

(1) Ammonium Carboxylate Amphoterics: Examples of such amphoteric surfactants include, but are not limited to: certain betaines such as cocobetaine and cocamidopropyl betaine; monoacetates such as sodium lauroamphoacetate; diacetates such as disodium lauroamphoacetate; amino- and alkylamino-propionates such as lauraminopropionic acid.

(2) Ammonium Sulfonate Amphoterics: These classes of amphoteric surfactants are often referred to as "sultaines" or "sulfobetaines" for example, cocamidopropylhydroxysultaine.

(C) Nonionic Surfactants: Surfactants of the nonionic type that may be particularly useful include:

(1) Polyethylene oxide extended sorbitan monoalkylates (i.e. Polysorbates); (2) Polyalkoxylated alkanols; (3) Polyalkoxylated alkylphenols include polyethoxylated octyl or nonyl phenols having HLB values of at least about 14, which are commercially available under the trade designations ICONOL and TRITON; (4) Polaxamers. Surfactants based on block copolymers of ethylene oxide (EO) and propylene oxide (PO) may also be effective. Both EO-PO-EO blocks and PO-EO-PO blocks are expected to work well as long as the HLB is at least about 14, and preferably at least about 16. Such surfactants are commercially available under the trade designations PLURONIC and TETRONIC from BASF; (5) Polyalkoxylated esters—Polyalkoxylated glycols such as ethylene glycol, propylene glycol, glycerol, and the like may be partially or completely esterified, i.e. one or more alcohols may be esterified, with a ($C_8$ to $C_{22}$) alkyl carboxylic acid. Such polyethoxylated esters having an HLB of at least about 14, and preferably at least about 16, may be suitable for use in compositions of the present invention; (6) Alkyl Polyglucosides—This includes glucopon 425, which has a ($C_8$ to $C_{16}$) alkyl chain length. Other possible non-ionic surfactants such as Decylglycoside compounds may be employed and are available as Plantaren from BASF, and Oramix from SEPPIC.

(D) Cationic Surfactants: Surfactants of the cationic type that may be useful include but are not limited to, primary amines, secondary amines, tertiary amines, quaternary amines, alkanolamines, mono-alkyl alkanolamines, di-alkyl alkanolamines, tri-alkyl alkanolamines, alkyl mono alkanolamines, alkyl di-alkanolamines, alkylamines, mono-alkyl amines, di-alkyl amines, tri-alkylamines, alkoxylated amines, alkyl and aryl amine alkoxylates, methoxylated alkylamines, ethoxylated alkylamines, alkoxylated alkanolamines, alkyl alkanolamines, alkoxylated ethylene diamine derivatives, alkyl/aryl/arylalkyl amine oxides. Preferred cationic surfactants of the present invention include, but are not limited to, (a) alkyl alkanolamines; and (b) alkyl tertiary amines. Additional information on useful cationic surfactants for the purpose of present invention is set forth in McCutcheon's Detergents and Emulsifiers, North American Ed., 1982 and Kirk-Othmer, Encyclopedia of Chemical Technology, $3^{rd}$ Ed., Vol. 22, pp. 346-387, the contents of which are incorporated herein by reference.

Suitable emulsifiers include the following classes of ethers and esters: ethers of polyglycols and of fatty alcohols, esters of polyglycols and of fatty acids, ethers of polyglycols and of fatty alcohols which are glycosylated, esters of polyglycols and of fatty acids which are glycosylated, ethers of $C_{12-30}$ alcohols and of glycerol or of polyglycerol, esters of $C_{12-30}$ fatty acids and of glycerol or of polyglycerol, ethers of oxyalkylene-modified $C_{12-30}$ alcohols and of glycerol or polyglycerol, ethers of $C_{12-30}$ fatty alcohols comprising and of sucrose or of glucose, esters of sucrose and of $C_{12-30}$ fatty acids, esters of pentaerythritol and of $C_{12-30}$ fatty acids, esters of sorbitol and/or of sorbitan and of $C_{12-30}$ fatty acids, ethers of sorbitol and/or of sorbitan and of alkoxylated sorbitan, ethers of polyglycols and of cholesterol, esters of $C_{12-30}$ fatty acids and of alkoxylated ethers of sorbitol and/or sorbitan, and combinations thereof. Linear or branched type silicone emulsifiers may also be used. Particularly useful polyether modified silicones include KF-6011, KF-6012, KF-6013, KF-6015, KF-6015, KF-6017, KF-6043, KF-6028, and KF-6038 from Shin-Etsu. Also particularly useful are the polyglycerolated linear or branched siloxane emulsifiers including KF-6100, KF-6104, and KF-6105 from Shin-Etsu. Emulsifiers also include emulsifying silicone elastomers. Suitable emulsifying silicone elastomers may include at least one polyalkyl ether or polyglycerolated unit.

The personal care composition of present application can be preserved by adding minor quantity of preservatives to the compositions. Such preservatives can be selected from, but are not limited to triazoles, imidazoles, naphthalene derivatives, benzimidazoles, morphline derivatives, dithiocarbamates, benzisothiazoles, benzamides, boron compounds, formaldehyde donors, isothiazolones, thiocyanates, quaternary ammonium compounds, iodine derivates, phenol derivatives, micobicides, pyridines, dialkylthiocarbamates, nitriles, parabens, benzoic acid, sorbic acid, salicylic acid, alkyl parabens and salts thereof.

Suitable antioxidants may be added to facilitate the enhanced shelf-life of the personal care composition. Exemplary antioxidants that can be used include vitamins such as vitamin E, vitamin E acetate, vitamin C, vitamin A, and vitamin D, and derivatives thereof. Additional exemplary antioxidants include but are not limited to propyl, octyl and dodecyl esters of gallic acid, butylated hydroxyanisole (BHA), butylated hydroxytoluene (BHT), and nordihydroguaiaretic acid. In general, the required amount of antioxidant for the present composition is in the range of about 0.2 wt. % to about 2 wt. %, and can be provided in an amount of about 0.5 wt. % to about 1.5 wt. %, based on the total weight of the composition.

The preferred fatty substance based excipient for the present application include fatty alcohols, natural and synthetic waxes, ceramides, mineral oils, vegetable oils, animal oils, synthetic oils. The other preferred fatty substance are isododecane, hydrogenated polyisobutene, squalane, isononyl isononanoate, cyclotetra- and—pentadimethicones, phenyltrimethicone, ethylene homopolymers, ethoxylated fats and oils, fluoroalkanes, seracite, shea butter, arachidyl propionate alone or in combination. For the definition of waxes, mention may be made, for example, of P. D. Dorgan, Drug and Cosmetic Industry, December 1983, pp. 30-33.

The preferred waxes of the present application would include microcrystalline waxes, carnauba wax, candelilla wax, esparto wax, paraffin wax, ozokerite. It is also considered to use plant waxes such as olive tree wax, rice wax, fruit waxes, hydrogenated jojoba wax or the absolute waxes of flowers such as the essential wax of blackcurrant flower sold by the company Bertin (France), animal waxes such as beeswaxes, or modified beeswaxes; other waxes or waxy starting materials which can be used according to this application are, in particular, marine waxes and polyethylene waxes or polyolefins.

The animal or plant oils are preferably chosen from sunflower oil, corn oil, soybean oil, avocado oil, jojoba oil, marrow oil, Argan oil, grapeseed oil, sesame oil, hazelnut oil, fish oils, glyceryl tricaprocaprylate, or plant or animal oils of formula $R_1COOR_2$ in which $R_1$ represents a higher fatty acid residue containing from 7 to 29 carbon atoms and $R_2$ represents a linear or branched hydrocarbon-based chain containing from 3 to 30 carbon atoms, particularly alkyl or alkenyl, for example purcellin oil or liquid jojoba wax. Further, it is also possible to use natural or synthetic essential oils such as, for example, eucalyptus oil, lavandin oil, lavender oil, vetiver oil, *Litsea cubeba* oil, lemon oil, sandalwood oil, rosemary oil, camomile oil, savory oil, nutmeg oil, cinnamon oil, hyssop oil, caraway oil, orange oil, geraniol oil, cade oil, almond oil, argan oil, avocado oil, olive oil, sun flower oil, cedar oil, wheat germ oil and bergamot oil.

The compounds of ceramide type are natural or synthetic ceramides and/or glycoceramides and/or pseudoceramides and/or neoceramides. The ceramide based type of compounds are described in detail in various patent prior arts, for example, DE4424530, DE 4424533, DE4402929, DE4420736, WO95/23807, WO94/07844, EP-A-0646572, WO 95/16665, FR-2673179, EP-A-0227994, WO94/07844, WO94/24097 and WO94/10131, the teachings of which are included herein by way of reference in its entirety.

Moisturizers employed in the present invention would include glycols, glycerols, propylene glycol, diethylene glycol monoethyl ether, sorbitol, sodium salt of pyroglutamic acid, glycerol, glycerol derivatives, glycerin, trehalose, sorbitol, maltitol, dipropylene glycol, 1,3-butylene glycol, sodium hyaluronate, and the like.

Further, it is known that moisturizers that bind well with water, thereby retaining it on the hair surface is called humectants. Examples of humectants which can be incorporated into a product of the present application are glycerine, propylene glycol, polypropylene glycol, polyethylene glycol, lactic acid, sodium lactate, pyrrolidone carboxylic acid, urea, phospholipids, collagen, elastin, ceramides, lecithin sorbitol, PEG-4, and mixtures thereof. Additional suitable moisturizers are polymeric moisturizers that belong to water soluble and/or water swellable in nature. Polysaccharides such as hyaluronic acid, chitosan can also be employed along with moisturizers of the present application as binder to enhance their property.

The preferred solvent of the present application may consist of water, a cosmetically acceptable solvent, or a blend of water and a cosmetically acceptable solvent, such as a lower alcohol composed of $C_1$ to $C_4$, such as ethanol, isopropanol, t-butanol, n-butanol, alkylene glycols such as propylene glycol, and glycol ethers. However, the compositions of the invention can be anhydrous. The most preferred solvents of the present application would include water, ethanol and/or iso-propanol.

It is contemplated to employ other suitable solvents for preparing products of the present application would include but not limited to linear and branched $C_1$-$C_6$ alcohols, such as ethanol, propanol, isopropanol, butanol, hexanol, and mixtures thereof; aromatic alcohols, such as benzyl alcohol, cycloaliphatic alcohols, such as cyclohexanol, and the like; saturated $C_{12}$-$C_{30}$ fatty alcohol, such as lauryl alcohol, myristyl alcohol, cetyl alcohol, stearyl alcohol, behenyl alcohol, and the like. Non-limiting examples of polyols include polyhydroxy alcohols, such as glycerin, propylene glycol, butylene glycol, hexylene glycol, $C_2$-$C_4$ alkoxylated alcohols and $C_2$-$C_4$ alkoxylated polyols, such as ethoxylated, propoxylated, and butoxylated ethers of alcohols, diols, and polyols having about 2 to about 30 carbon atoms and 1 to about 40 alkoxy units, polypropylene glycol, polybutylene glycol, and the like. Non-limiting examples of non-aqueous auxiliary solvents include silicones, and silicone derivatives, such as cyclomethicone, and the like, aliphatic solvents such as cyclohexane and heptane, ketones such as acetone and methyl ethyl ketone, and mixtures thereof; ethers such as diethyl ether, dimethoxymethane, and mixtures thereof, natural and synthetic oils and waxes, such as vegetable oils, plant oils, animal oils, essential oils, mineral oils, $C_7$-$C_{40}$ isoparaffins, alkyl carboxylic esters, such as ethyl acetate, amyl acetate, ethyl lactate, and the like, jojoba oil, shark liver oil, and the like.

The preferred neutralizing agents that can be included in the product of the present application to neutralize components such as e.g. an emulsifier or a foam builder/stabilizer include but are not limited to alkali hydroxides such as a sodium and potassium hydroxide; organic bases such as methylethylamine (MEA), ammonia, aminoalcohols, lithium hydroxide, diethanolamine (DEA); triethanolamine (TEA), aminomethyl propanol, and mixtures thereof; amino acids such as arginine and lysine and any combination of any foregoing. The neutralizing agent can be present in an amount of about 0.01 wt. % to about 8 wt. %, preferably, 1 wt. % to about 5 wt. %.

Other preferred pH adjusting agents would include alkaline pH adjusting agents include alkali metal hydroxides, such as sodium hydroxide, and potassium hydroxide; ammonium hydroxide; organic bases, such as triethanolamine, diisopropylamine, dodecylamine, diisopropanolamine, aminomethyl propanol, cocamine, oleamine, morpholine, triamylamine, triethylamine, tromethamine (2-amino-2-hydroxymethyl)-1,3-propanediol), and tetrakis(hydroxypropyl)ethylenediamine; and alkali metal salts of inorganic acids, such as sodium borate (borax), sodium phosphate, sodium pyrophosphate, and the like, and mixtures thereof. Acidic pH adjusting agents can be organic acids, including amino acids, and inorganic mineral acids. Non-limiting examples of acidic pH adjusting agents include acetic acid, citric acid, fumaric acid, glutamic acid, glycolic acid, hydrochloric acid, lactic acid, nitric acid, phosphoric acid, sodium bisulfate, sulfuric acid, tartaric acid, and the like, and mixtures thereof.

Suitable buffering agents include but are not limited to alkali or alkali earth carbonates, phosphates, bicarbonates, citrates, borates, acetates, acid anhydrides, succinates and the like, such as sodium phosphate, citrate, borate, acetate, bicarbonate, and carbonate.

Examples of anti-dandruff agents that can be used are cimbazole, octopirox and zinc pyrithione, salicylic acid, elemental sulfur, selenium dioxide, and the azole antimycotics.

According to one important embodiment of the present application, it is contemplated to employ natural plant extracts showing hair conditioning, restructuring effects, growing effects, can be used in the conditioners. Those are preferably the extracts from almond, coconut, mango, peach, lemon, wheat, rosemary, apricot, algae, grapefruit, sandalwood, lime orange, *Acacia concinna, Butea parviflora, Butea superb, Butea frondosa* and/or *Aloe Vera*. The extracts of these plants are obtained from seeds, roots, stem, leaves, flowers, bark, fruits, and/or whole plant.

According to one important embodiment of the present application, it is contemplated to employ at least one organic UV filters which can filter out UV rays can be selected from hydrosoluble or liposoluble filters, whether siliconated or nonsiliconated, and mineral oxide particles, the surface of which may be treated.

Hydrosoluble organic UV filters can be chosen from para-amino benzoic acid and its salts, anthranilic acid and its salts, salicylic acid and its salts, hydroxy cinnamic acid and its salts, sulfonic derivatives of benzothiazoles, benzimidizoles, benzoxazoles and their salts, sulfonic derivatives of benzophenone and their salts, sulfonic derivatives of benzylidene camphor and their salts, derivatives of benzylidene camphor substituted by a quaternary amine and their salts, derivatives of phthalydene-camphosulfonic acids and their salts, sulfonic derivatives of benzotriazole, and mixtures thereof.

Hydrophilic polymers which have light-protective qualities against UV rays can be used. These include polymers containing benzylidene camphor and/or benzotriazole groups.

Suitable liposoluble organic UV filters would include but are not limted to derivatives of para-aminobenzoic acid, such as the esters or amides of para-aminobenzoic acid; derivatives of salicylic acid; derivatives of benzophenone; derivatives of dibenzoyl methane; derivatives of diphenyl acrylates; derivatives of benzofurans; UV filter polymers containing one or more silico-organic residues; esters of cinnamic acid; derivatives of camphor; derivatives of trianilino-s-triazine; the ethylic ester urocanic acid; benzotriazoles; derivatives of hydroxy phenyl triazine; bis-resorcinol-dialkyl amino triazine; and mixtures thereof.

The liposoluble (or lipophilic) organic UV filter according to the invention can be chosen from octyl salicylate; 4-tert-butyl-4'-methoxy dibenzoyl methane; octocrylene; 4-methoxy cinnamate; 2-ethylhexyl [2-ethylhexyl 4-methoxycinnamate]; and 2-(2H-benzotriazol-2-yl)-4-methyl-6-[2-methyl-3-[1,3,3,3-tetramethyl-1-[(trimethyl silyl)oxy] disiloxanyl]propynyl] phenol.

Other UV filters particularly preferred for use herein are derivatives of benzophenones such as 2-hydroxy-4-methoxy benzophenone-5-sulfonic acid, 2-hydroxy-4-methoxy benzophenone, derivatives of benzalmalonates such as poly dimethyl/methyl (3(4-(2,2-bis-ethoxy carbonyl vinyl)-phenoxy)-propenyl) siloxane, derivatives of benzylidene camphor such as b-b'camphosulfonic-[1-4 divinylbenzene] acid and derivatives of benzimidazole such as 2-phenyl-benzimidazol-5-sulfonic acid.

Water-insoluble UV filters also include various mineral oxides. The mineral oxides can be selected from among titanium oxides, zinc oxides, and cerium oxides. The mineral oxides can be used in the form of ultrafine nanoparticles.

Preferred UV filters include Escalol HP-610 (dimethyl-pabamido propyl laurdimonium tosylate and propylene glycol stearate) and Crodasorb HP (polyquaternium 59).

The coloring agents, colorants or dyes used herein include natural foods colors and dyes suitable for food, drug and cosmetic applications. These colorants are also known as FD & C, and D&C dyes and lakes and are preferably water-soluble in nature. A full recitation of all FD&C and D&C dyes and their corresponding chemical structures may be found in the Kirk-Othmer Encyclopedia of Chemical Technology, Volume 5, pages 857-884, which text is accordingly incorporated herein by reference. These coloring agents may be incorporated in amount up to about 3%, more particularly up to about 2%, and in some cases less than about 1% by weight of the personal care compositions.

In preparing personal care composition herein, it is preferred to add suitable thickening agents wherever required to provide a desirable consistency to the appropriate formulation. Examples of useful thickening agents include carboxyvinyl polymers, carrageenan, hydroxyethyl cellulose, hydrophobically modified hydroxy-ethyl-cellulose, laponite and water soluble salts of cellulose ethers such as sodium carboxymethylcellulose and sodium carboxymethyl hydroxyethyl cellulose, copolymers of lactide and glycolide monomers, carbomers. Natural gums such as gum karaya, xanthan gum, gum arabic, Guars, HP Guars, and gum tragacanth can also be used. Some thickening agents, however, except polymeric polyether compounds, e.g., polyethylene or polypropylene oxide (MW 300 to 1,000,000), capped with alkyl or acyl groups containing 1 to about 18 carbon atoms. Carbomers are commercially available from Lubrizol as the Carbopol Series. Particularly preferred carbopols include Carbopol 934, 940, 941, 956, 980, 981, 1342, 1382, 2984, 5984, Aqua, Ultrez, ETD polymers, Pemulen polymers, and mixtures thereof. Thickening agents are usually present in an amount from about 0.1% to about 25% by weight of the disinfectant/cleaning concentrate composition. However, the preferred amount of thickening agent for the present composition is the range of about 0.01-5.0% by weight, preferably about 0.05-2.0%.

The term "sequestering agent" or "chelating agent" as used herein relates to a compound which is capable of bonding or complexing a metal ion between two or more atoms of the compound, thereby neutralizing or controlling harmful effects of such metal ions. Wherein holding or bonding of a metal ion is through combination of one or more different types of bonds including coordination and/or ionic bonds. The suitable organic or inorganic sequestering or chelating for the purposes of the present application is selected from the group comprising polyols, gluconates, sorbitals, mannitols, carbonates, hydroxamates, catechols, α-amino carboxylates, alkanolamines, metal-ion sequestrants, hydroxy-carboxylic acids, aminocarboxylic acids, amino polycarboxylic acids, polyamines, polyphosphates, phosphonic acids, crown ethers, amino acids, polycarboxylic acids, cyclodextrin, phosphonates, polyacrylates or polymeric polycarboxylates, condensed phosphates. Further, the information on sequestering and chelating agents is disclosed in T. E. Furia, CRC Handbook of Food Additives, $2^{nd}$ Edition, pp. 271-294 (1972), and M. S. Peterson and A. M. Johnson (Eds.), Encyclopedia of Food Science, pp. 694-699 (1978) are incorporated herein by reference in its entirety.

The pH of the composition can be controlled within any desired range according to the type and purpose of the formulation. In order to attain the desired pH range, various pH modifiers may be employed in the present composition. Specific examples of basic pH modifiers are ammonia; sodium, potassium, and lithium hydroxide; sodium, potassium, and lithium meta silicates; monoethanolamine; triethylamine; isopropanolamine; diethanolamine; and triethanolamine. The suitable acidic pH modifying agents that can be employed in the present application include, but are not limited to, mineral acids, carboxylic acids and polymeric acids. Specific examples for mineral acids are hydrochloric acid, nitric acid, phosphoric acid, and sulfuric acid. Examples for appropriate carboxylic acids are citric acid, glycolic acid, lactic acid, maleic acid, malic acid, succinic acid, glutaric acid, benzoic acid, malonic acid, salicylic acid, gluconic acid, and mixtures thereof. Examples for suitable polymeric acids include straight-chain poly(acrylic) acid and its copolymers (e.g., maleic-acrylic, sulfonic-acrylic, and styrene-acrylic copolymers), cross-linked polyacrylic acids having a molecular weight of less than about 250,000, poly(methacrylic) acid, and naturally occurring polymeric acids such as carageenic acid, carboxymethyl cellulose, and alginic acid.

The desired pH of the personal care composition is in the range of from about 3 to about 13, and in some embodiment, it is preferably between about 4 to about 8. The utility levels of the pH modifying agent may be present in an effective amount required to achieve the desired pH level.

A perfume or fragrance obtained from natural or synthetic source can be employed in the present personal care composition. The fragrance may be used along with a suitable solvent, diluents or carrier. Fragrances may be added in any conventionally known method, for example, admixing to a composition or blending with other ingredients used to form a composition, in amounts which are found to be useful to increase or impart the desired scent characteristics to the disinfectant or cleaning compositions. Fragrances for the present application can be one or more selected from the following non-limiting group of compounds such as essential oils, absolutes, resinoids, resins, concretes, hydrocarbons, alcohols, aldehydes, ketones, ethers, acids, esters, acetals, ketals, nitriles, including saturated and unsaturated compounds and aliphatic, carbocyclic and heterocyclic compounds.

According to one embodiment of the present application, the conditioning and/or styling composition optionally comprises any silicones which are known to a person skilled in the art, such silicones may be present in the form of oils, waxes, resins, or gums. Silicones for the present invention can be selected from Encyclopedia of Polymer Science and Engineering, vol. 15, 2d ed., pp 204-308, John Wiley & Sons, Inc. (1989), is incorporated herein by reference. Non-limiting examples of suitable silicone conditioning agents, and optional suspending agents for the silicone, are described in detail in U.S. Reissue Pat. No. 34584, U.S. Pat. Nos. 5,104,646, and 5,106,609 and can be readily referred for the purposes of the invention.

Suitable silicones for the present application are duly disclosed in U.S. Pat. Nos. 2,826,551, 3,964,500, 4,364,837, British Patent No. 849433, EP-A-0 582152, WO 93/23009, and Silicon Compounds, Petrarch Systems, Inc. (1984), all of which are incorporated herein by reference The suitable silicones of the present application would include but are not limited to polyorganosiloxanes, polyalkyl siloxanes, polyaryl siloxanes, polyalkyl aryl siloxanes, silicone gums and resins, and polyorgano siloxanes modified by organofunctional groups, and mixtures thereof. Suitable polyalkyl siloxanes include polydimethyl siloxanes with terminal trimethyl silyl groups or terminal dimethyl silanol groups (dimethiconol) and polyalkyl ($C_1$-$C_{25}$) siloxanes. Suitable polyalkyl aryl siloxanes include polydimethyl methyl phenyl siloxanes and polydimethyl diphenyl siloxanes, linear or branched. The silicone gums suitable for use herein include polydiorganosiloxanes preferably having a number-average molecular weight between 200,000 and 1,000,000, used alone or mixed with a solvent. Examples include polymethyl siloxane, polydimethyl siloxane/methyl vinyl siloxane gums, polydimethyl siloxane/diphenyl siloxane, polydimethyl siloxane/phenyl methyl siloxane and polydimethyl siloxane/diphenyl siloxane/methyl vinyl siloxanes. Suitable silicone resins include silicones with a dimethyl/trimethyl siloxane structure and resins of the trimethyl siloxysilicate type. The organo-modified silicones suitable for use in the invention include silicones such as those previously defined and containing one or more organofunctional groups attached by means of a hydrocarbon radical and grafted siliconated polymers. Particularly preferred are amino functional silicones. The silicones may be used in the form of emulsions, nano-emulsions, or micro-emulsions.

Another embodiment of the present application provides a method for treating or fixing damaged keratin substrate comprising contacting said keratin substrate with an effective amount of personal care composition comprising a conditioning and/or styling terpolymer/tetrapolymer of (i) about 50 wt. % to 97 wt. % of diallyl dimethyl ammonium chloride (DADMAC), a cationic monomer; (ii) about 1 wt. % to 30 wt. % of an anionic monomer selected from the group consisting of (a) acrylic acid (AA), (b) acrylamido methylpropyl sulfonate (AMPS) or (c) sodium methyl allyl sulfonate (SMAS); and (iii) about 0.1 wt. % to 20 wt. % of a hydrophobic monomer selected from the group consisting of (a) polyoxyethylene (PEG)-18-behenylether methacrylate (BEM) or (b) stearyl acrylate (SA), and wherein, said terpolymer has a cationic degree of substitution (Cat-DS) of greater than about 0.001 units, and wherein the cationic charge density is in the range of about 1 meq/g to about 6.5 meq/g.

Yet another embodiment of the present application provides a method for washing or caring damaged or undamaged keratin substrate comprising applying an effective amount of composition comprising a conditioning and/or styling terpolymer/tetrapolymer of (i) about 50 wt. % to 97 wt. % of diallyl dimethyl ammonium chloride (DADMAC), a cationic monomer; (ii) about 1 wt. % to 30 wt. % of an anionic monomer selected from the group consisting of (a) acrylic acid (AA), (b) acrylamido methylpropyl sulfonate (AMPS) or (c) sodium methyl allyl sulfonate (SMAS); and (iii) about 0.1 wt. % to 20 wt. % of a hydrophobic monomer selected from the group consisting of (a) polyoxyethylene (PEG)-18-behenylether methacrylate (BEM) or (b) stearyl acrylate (SA), and wherein, the ter/tetra polymer has a cationic degree of substitution (Cat-DS) of greater than about 0.001 units, and wherein the cationic charge density is in the range of about 1 meq/g to about 6.5 meq/g.

According to one important embodiment of the is application, there is provided a method of protecting dyed hair color from fading or wash-out during exposure to air and/or shampooing which comprising contacting/treating said dyed hair with an effective amount of personal care composition of claim 1 comprising: (a) a conditioning and/or styling ter/tetra polymer of (i) about 50 wt. % to 97 wt. % of diallyl dimethyl ammonium chloride (DADMAC); (ii) about 1 wt. % to 30 wt. % of an anionic monomer selected from the group consisting of (a) acrylic acid (AA), (b) acrylamido methylpropyl sulfonate (AMPS) or (c) sodium methyl allyl sulfonate (SMAS); and (iii) about 0.1 wt. % to 20 wt. % of a hydrophobic monomer selected from the group consisting of (a) polyoxyethylene (PEG)-18-behenylether methacrylate (BEM), (b) stearyl acrylate (SA) or (c) Lauryl ethoxylated methacrylate (LEM); and wherein said ter/tetra polymer has a cationic degree of substitution (Cat-DS) of greater than about 0.001 units, and wherein the cationic charge density is in the range of about 1 meq/g to about 6.5 meq/g. The above disclosed method is capable of protecting hair dyes that are disclosed in US 20050226838 and which included herein in its entirety.

The effective amount of terpolymer or tetrapolymer required for a personal care composition to treat, fix or wash a damaged keratin substrate is in the range of from about 0.01 wt. % to about 5.0 wt. %, and preferably in the range of from about 0.2 wt. % to about 3.0 wt. % of the total composition.

According to one embodiment of the present application, it is contemplated to employ at least one ter/tetra polymer of present application and at least one commercially available conditioning polymer. Suitable commercially available conditioning polymers are selected from the following non-limiting group of examples which include polymeric quaternary ammonium salts such as, without being limited thereto, polyquaternium-7, a polymeric quaternary ammonium salt of acrylamide and dimethyl diallylammonium chloride monomers (such as MACKERNIUMTM-007, McIntyre Group, Ltd.); polyquaternium-10, a polymeric quaternary ammonium salt of hydroxyethylcellulose reacted with a trimethylammonium substituted epoxide (such as the UCARE® Polymers JR, LK, LR, SR series, Amerchol and CELQUAT® SC series, Akzo Nobel); polyquaternium-39, a polymeric quaternary ammonium salt of acrylic acid, diallyl dimethylammonium chloride and acrylamide (such as the MERQUAT® and MERQUAT® Plus polymers, Ondeo Nalco); quaternized derivatives of natural gums, e.g., guar hydroxypropyltrimonium chloride (such as the N-HANCE® and Supercol® polymers, Ashland Inc.), and the like.

Further, certain aspects of the present invention are illustrated in detail by way of the following examples. The examples are given herein for illustration of the invention and are not intended to be limiting thereof.

EXAMPLE 1

Wet Combability Conditioner Application—Long lasting effect of DADMAC tetrapolymer [DADMAC/AA/BEM/VCAP (95.3/2.5/2/0.2)]

Figure 1:
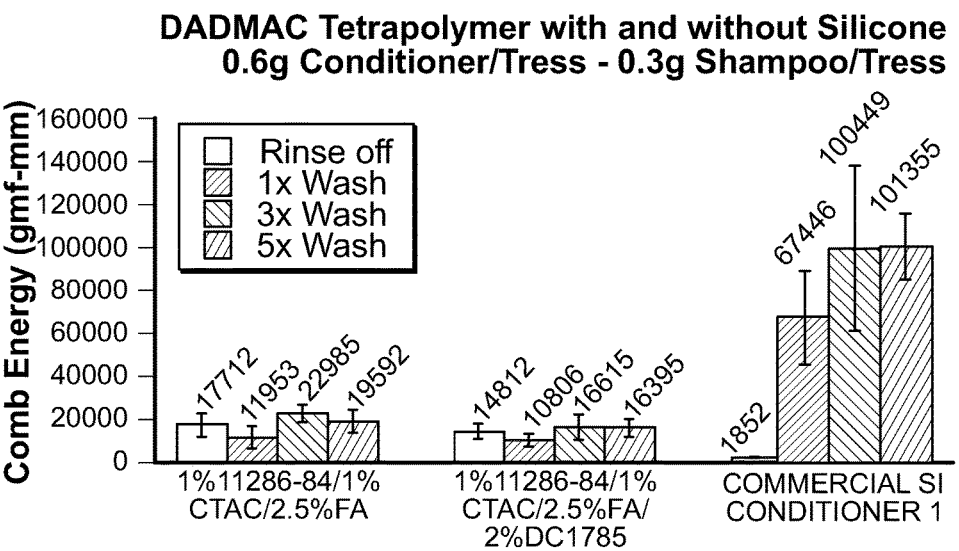
FIG. 1 shows wet combability of tetra polymer and other commercial conditioners with/without silicones.

Combing Measurements with Texture Analyzer: The combing measurement of the hair tresses treated with conditioner composition comprising DADMAC tetrapolymer (Table 1) was done on a texture analyzer without manually detangling the hair. The energy needed to comb the tress was listed as gf-mm. For every measurement, 3 bleached hair tresses were used and the average was calculated. To measure durable conditioning the tress was first treated with 0.2 g/g hair conditioner, which is then rinsed off and the comb energy is measured. After the measurement the hair is washed with non-conditioning shampoo once, comb energy was measured then 3 and 5 times. No conditioner was applied in between. The results were demonstrated in FIG. 1.

In comparison to a commercial silicone containing conditioner the conditioner with DADMAC tetrapolymer showed with and without silicone excellent long-lasting performance (here as wet combability) after rinse off and 1/3/5 times washed with non-conditioning shampoo (shampoo base of 2% CAPB and 12% SLES).

TABLE 1

Conditioner Compositions used for combability measurement

| Formulation | Z331-11A | Z331-11D |
|---|---|---|
| Aqua | q.s | q.s |
| DADMAC/AA/BEM/VCAP | 1 | 1 |
| Cetyl trimethyl amonium chloride | 1 | 1 |
| Citric Acid | 0.13 | 0.13 |
| Cetearyl Alcohol | 2.5 | 2.5 |
| Dimethiconol (and) TEA-Dodecylbenzenesulfonate | — | 2 |
| Hydroxyethylcellulose 250 HHR | 1 | 1 |
| Methylisothiazolinone (and) Phenylpropanol (and) Propylene Glycol | 0.5 | 0.5 |
| Commercial Si conditioner 1 | Aqua, Cetearyl Alcohol, Behentrimonium chloride, CetylEsters Lactic acid, Trideceth-6, Chlorhexidine Digluconate, Limonene, Linalool, Benzyl Salicylate Benzyl alcohol, Amodimethicone, Isopropylalcohol, 2-Oleamido-1,3-Octanediol, ButylphenylMethylpropional, | |

TABLE 1-continued

Conditioner Compositions used for combability measurement

| Formulation | Z331-11A | Z331-11D |
|---|---|---|
| | Potassium Hydroxide, Cetrimmonium-chloride, Hexyl Cinnamal, Parfum | |

EXAMPLE 2

Hydrophobicity Determination by Contact Angle Measurement

Contact angle is the indication of the surface hydrophobicity of hair. The immediate and long-lasting hydrophobicity of the tetra polymers were studied by measuring the contact angle after several washes with a tetrapolymer containing shampoo. The method is as follows: (i) A portion of the hair tress was stretched on a specially designed plate so that the fibers were suspended together in space to form a "single" surface (ii) A droplet of Deionized water was delivered from a syringe onto the fiber surface. Droplet mass is ~0.008 g, (iii) Images were collected at intervals of 1 s or 10 s.

Figure 2:
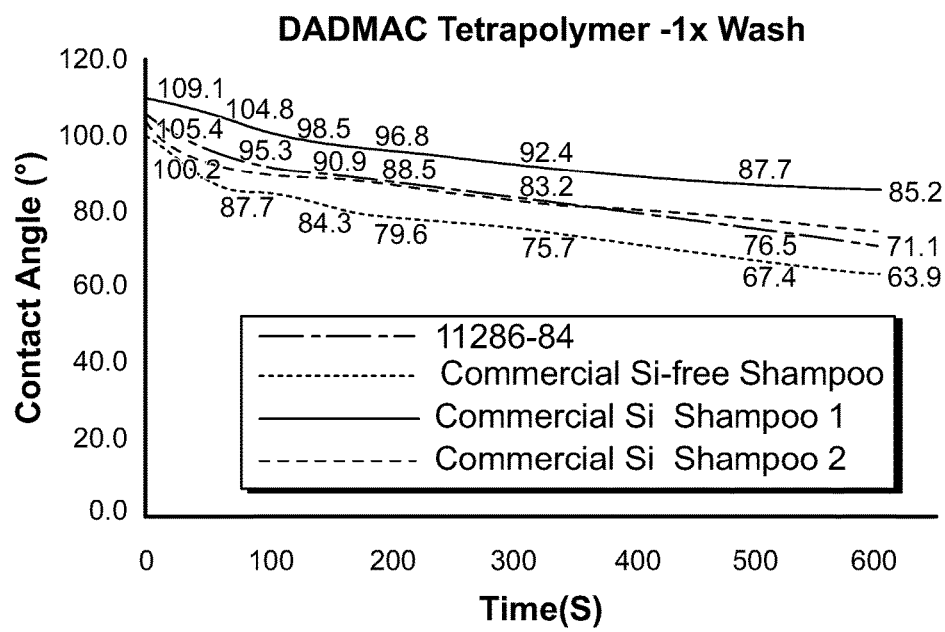
FIG. 2 shows a hydrophobicity evaluation of tetra polymers after 1 wash.
Figure 3:
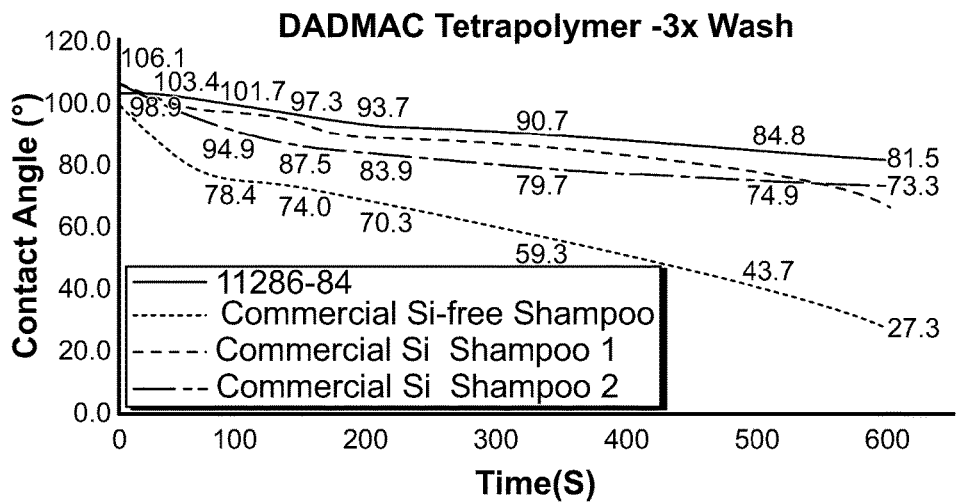
FIG. 3 shows a hydrophobicity evaluation of tetra polymers after 3 washes.

The higher the contact angle the more hydrophobic is the surface. The undamaged virgin brown hair is naturally hydrophobic, but all the chemical treatments such as bleaching reduce the hydrophobicity of the hair. Contact angle of virgin hair is about 110 which is reduced to 85 by bleaching. Also the water droplet applied to the hair surface is absorbed in 60 s. On virgin hair, the droplet can stay several hours. The results demonstrates (FIG. 2 and FIG. 3) the influence of (0.2 wt %) tetra polymers supplied from a shampoo on the contact angle. It is concluded that the repetitive treatment with tetrapolymer containing shampoos leads to a restoration of hydrophobicity of the damaged hair close to the level of virgin hair. The hydrophobicity test results are provided in Table 1, FIG. 2 and FIG. 3.

In comparison to fully formulated commercial shampoos with conditioning polymers and silicones and without silicones, DADMAC tetrapolymer containing shampoo shows the best lastingness benefits, being after three hair washes superior to the commercial shampoos.

EXAMPLE 3

Wet Combability Shampoo Composition

Figure 4:
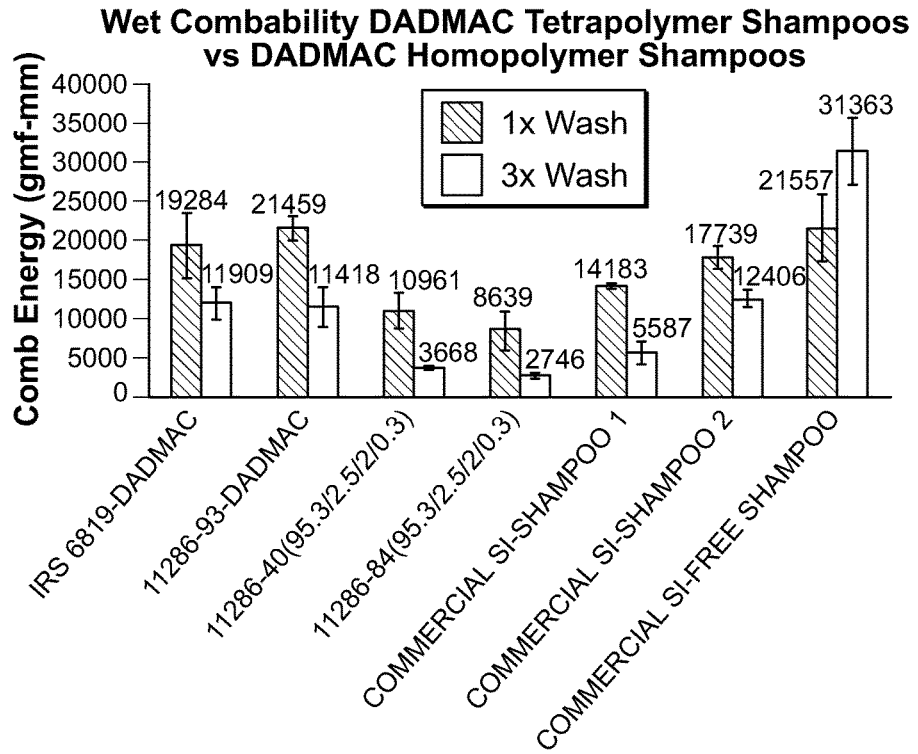
FIG. 4 shows wet combability evaluation of DADMAC tetrapolymer shampoo.

The combing measurement of the hair tresses treated with tetra polymer containing shampoo was done on Instron device. The energy needed to comb the tress was listed as gf-mm. For every measurement 3 bleached hair tresses were used and the average was calculated. To measure durable conditioning the tress is first treated with 0.1 g/g hair shampoo, which is then rinsed off and the comb energy is measured. The tress was washed 2 more times and the comb energy was again measured. The results of wet comb energy after 1 and 3 washes are disclosed in FIG. 4 and Table 2 for shampoo compositions with DADMAC homopolymer (PQ6) and DADMAC tetrapolymer.

From the results of wet combability for the tetrapolymer shampoo compositions, it is evident that the conditioning performance of tetra polymers shampoo is even better as compared to PQ6. The shampoos were applied on damaged hair 0.1 g grams per gram of bleached hair (1 hour bleached) and wet comb energies were measured after 1 and 3 and 5 times of washing with 0.1 grams per gram hair experimental shampoo. Both homopolymer and tetrapolymer containing shampoos were outperforming commercial silicone-free shampoo.

TABLE 2

Shampoo formulations for Wet combability and contact angle measurement

| Formulations | Code | 1 | 2 | 3 | 4 |
|---|---|---|---|---|---|
| Aqua | — | q.s. | q.s. | q.s. | q.s. |
| DADMAC/AA/BEM/VCAP (40%) | 11286-84 | 0.5 | — | — | — |
| DADMAC/AA/BEM/VCAP (40%) | 11286-40 | — | — | 0.5 | — |
| DADMAC homopolymer (40%) | IRS 6819 | — | 0.5 | — | — |
| DADMAC homopolymer (40%) | 11286-93 | — | — | — | 0.5 |
| Sodium Laureth ether sulfate, solids % | — | 12 | 12 | 12 | — |
| Cocamidopropyl Betaine, % solids | — | 2 | 2 | 2 | — |
| Preservative | — | 0.5 | 0.5 | 0.5 | — |
| Sodium Chloride | — | 2 | 2 | 2 | — |
| Commercial Shampoo Si free | Aqua, ALS, CAPB, Sodium Chloride, Niacinamide, sugar cane extract, Hydroxypropyl guar hydroxypropyltrimonium Chloride (Jaguar C162), *Camellia Sinensis* Extract | | | | |
| Commercial Si shampoo 1 | Water, Sodium Lauryl Sulfate, Sodium Laureth Sulfate, Sodium Chloride, Glycol Distearate, Laureth-4, Sodium Citrate, Sodium Xylenesulfonate, Fragrance, Dimethicone, Citric Acid, Sodium Benzoate, Tetrasodium EDTA, Trisodium Ethylenediamine Disuccinate, Polyquaternium-6, Panthenol, Panthenyl Ethyl Ether, Methylchloroisothiazolinone, Methylisothiazolinone | | | | |
| Commercial Si shampoo 2 | Water, Sodium Lauryl Sulfate, Sodium Laureth Sulfate, Cocamidopropyl Betaine, Glycol Distearate, Dimethicone, Sodium Citrate, Cocamide MEA, Sodium Xylenesulfonate, Fragrance, Citric Acid, Sodium Benzoate, Sodium Chloride, Guar Hydroxypropyltrimonium Chloride, Tetrasodium EDTA, Trisodium Ethylenediamine Disuccinate, Polyquaternium-6, Panthenol, Panthenyl Ethyl Ether, Methylchloroisothiazolinone, Methylisothiazolinone. | | | | |

When compared to the silicone-containing commercial PQ6 shampoos, the experimental shampoos were out performing the commercial fully formulated shampoos.

EXAMPLE 4

Sensory Evaluation

A trained panel of experts has evaluated the sensory properties of the treated hair tresses and the results were very much correlating with measured values e.g. comb energy values. Sensory properties are essential part of consumer acceptance. With the help of the sensory evaluation the long-term properties after multiple uses can be determined.

Tetra polymers were used at 0.2 wt % active in conjunction with 12 wt % $SLE_2S$, 2 wt % CAPB with water added to 100%. The simple shampoo formula was then applied to the hair at 0.3 g/g bleached Caucasian hair and washed and rinsed off. After drying at RT, it was evaluated. Then the procedure was repeated 2 more times and the samples were evaluated. The following test shampoos and market reference shampoos were compared with tetra polymers of the present application for the sensory evaluation (Table 3).

In wet state, after one wash evaluation of the wet performance of hair tresses demonstrated detangling property and rest of the properties were normal. However, after three hair tresses washes, there was a big difference in every performance evaluation parameters (Table 4) that was considered, except stickiness. These results demonstrated advantages of composition comprising DADMAC tetra polymer of the present application. The results are provided in FIGS. 5 and 6.

TABLE 3

| Test Shampoos used for sensory evaluation | | | | | |
|---|---|---|---|---|---|
| Formulations | Code | 1 | 2 | 3 | |
| Aqua | — | q.s. | q.s. | q.s. | |
| DADMAC/AA/BEM/VCAP (40%) | 11286-84 | 0.5 | — | — | |
| DADMAC/AA/BEM/VCAP (40%) | 11286-46 | — | 0.5 | — | |
| DADMAC/AA/BEM/VCAP (40%) | 11286-44 | — | — | 0.5 | |
| Sodium Laureth ether sulfate, solids % | — | 12 | 12 | 12 | |
| Cocamidopropyl Betaine, % solids | — | 2 | 2 | 2 | |
| Preservative | — | 0.5 | 0.5 | 0.5 | |
| Sodium Chloride | — | 2 | 2 | 2 | |
| Commercial Si free Shampoo | Aqua, ALS, CAPB, Sodium Chloride, Niacinamide, sugar cane extract, Hydroxypropyl guar hydroxypropyltrimonium Chloride *Camellia Sinensis* Extract | | | | |

TABLE 4

| | | Wet state after 1 wash and after 3 washes | | | | | | | |
|---|---|---|---|---|---|---|---|---|---|
| | | WET STATE | | | | | | | |
| | | 11286-46 | | 11286-84 | | 11286-44 | | Commercial silicon free shampoo | |
| | | Washing cycles | | | | | | | |
| Parameter | Description | 1 | 3 | 1 | 3 | 1 | 3 | 1 | 3 |
| Detangling Difficult - easy | Ease of detangling | 2.83 | 4.13 | 3.67 | 4.13 | 2.33 | 4.38 | 3.00 | 2.50 |
| Combability Difficult - easy | Ease of combing down hair shaft | 3.13 | 3.88 | 3.25 | 4.38 | 2.75 | 4.38 | 3.00 | 2.00 |
| Stickiness | Run fingers down tress is it sticky | 3.38 | 3.75 | 3.25 | 3.50 | 3.13 | 3.63 | 3.63 | 3.75 |
| Slipperiness Drags - slips | Lack of drag or resistance as moving along hairs between fingers | 3.25 | 4.00 | 3.38 | 4.25 | 3.13 | 4.13 | 3.25 | 2.63 |
| Smoothness Drag - smooth | A rough, brittle texture | 3.38 | 4.25 | 3.13 | 4.50 | 3.13 | 4.50 | 3.13 | 2.50 |
| Coatedness | The hair is felt for any coated or unclean feel. | 4.00 | 3.38 | 4.00 | 3.75 | 4.00 | 3.25 | 4.25 | 3.00 |

TABLE 5

Dry state after 1 wash and after 3 washes

| | | \multicolumn{8}{c}{DRY STATE} | | | | | | | |
|---|---|---|---|---|---|---|---|---|---|
| | | 11286-46 | | 11286-84 | | 11286-44 | | Commercial silicon free shampoo | |
| | | \multicolumn{8}{c}{Washing cycles} | | | | | | | |
| Parameter | Description | 1 | 3 | 1 | 3 | 1 | 3 | 1 | 3 |
| Hydrophobicity | Absorption time of water droplets into hair | 4.00 | 3.00 | 4.50 | 5.00 | 4.50 | 5.00 | 2.00 | 1.00 |
| Sheen dull-shiny | Amount of reflected light | 3.50 | 3.83 | 3.67 | 4.00 | 3.17 | 4.00 | 3.17 | 4.00 |
| Detangling Difficult - easy | Ease of detangling | 3.50 | 4.25 | 3.88 | 4.63 | 3.75 | 4.13 | 3.00 | 3.63 |
| Combability Difficult - easy | Ease of combing down hair shaft | 4.25 | 4.13 | 3.88 | 4.50 | 3.75 | 4.25 | 2.25 | 2.75 |
| Fly away Much - none | Tendency of individual hairs to rebel each after 3 strokes of combing | 3.75 | 3.75 | 3.50 | 3.63 | 3.38 | 3.63 | 3.25 | 4.00 |
| Volume Low volume - full | Extend to which the hair appears full | 3.38 | 3.63 | 3.38 | 3.50 | 3.75 | 3.63 | 3.13 | 3.75 |
| Slipperiness Drags - slips | Lack of drag or resistance as moving along hairs between fingers | 3.50 | 4.13 | 3.75 | 4.25 | 3.50 | 4.25 | 2.63 | 3.75 |
| Smoothness Drag - smooth | A rough, brittle texture | 3.50 | 4.13 | 4.00 | 4.13 | 3.88 | 4.13 | 2.75 | 3.75 |
| Coatedness Coated - Non coated | The hair is felt for any coated or unclean feel. | 4.50 | 3.50 | 4.50 | 3.63 | 4.50 | 3.75 | 4.13 | 3.63 |
| Dryness Very dry - not dry | Feel devoid of moisture | 4.00 | 4.50 | 4.00 | 4.50 | 4.00 | 4.50 | 3.38 | 4.63 |

In case of dry state evaluation, the compositions comprising DADMAC tetrapolymer demonstrated better performance for most of the evaluation parameters after one wash of hair stresses, and wherein, the hydrophobicity detangling and combability showed better performance that are directly related to styleability and manageability of hair stresses. Whereas, after 3 washes of hair stresses, these advantages increased further. The results for dry state evaluation were given in Table 5 and FIGS. 7 and 8.

While this invention has been described in detail with reference to certain preferred embodiments, it should be appreciated that the present invention is not limited to those precise embodiments. Rather, in view of the present disclosure, which describes the current best mode for practicing the invention, many modifications and variations would present themselves to those skilled in the art without departing from the scope and spirit of this invention.

What is claimed is:

1. A conditioning and/or styling copolymer for a keratin substrate obtained from polymerizing:
   i. about 50 wt. % to 97 wt. % of diallyl dimethyl ammonium chloride (DADMAC);
   ii. about 1 wt. % to 20 wt. % of acrylic acid (AA);
   iii. about 0.1 wt. % to 20 wt. % of polyoxyethylene (PEG)-18-behenylether-methacrylate (BEM); and
   iv. about 0.1 wt. % to 10 wt. % of vinylcaprolactam (V-cap);
and wherein said co-polymer is a tetrapolymer having a cationic degree of substitution (Cat-DS) of greater than about 0.001 units, and wherein the cationic charge density is in the range of about 1 meq/g to about 6.5 meq/g.

2. The copolymer according to claim 1, wherein said keratin substrate is hair or skin.

3. The copolymer according to claim 1, wherein the average molecular weight of said tetra polymer is in the range of from about 75,000 to 1000,000 g/mol as determined by gel permeation chromatography.

4. The copolymer according to claim 1, wherein the average molecular weight of said tetra polymer ranges from about 120,000 to 500,000 g/mol as determined by gel permeation chromatography.

5. A process for preparing a conditioning and/or styling copolymer comprising polymerizing:
   i. about 50 wt. % to 97 wt. % of diallyl dimethyl ammonium chloride (DADMAC);
   ii. about 1 wt. % to 20 wt. % of acrylic acid (AA);
   iii. about 0.1 wt. % to 20 wt. % of polyoxyethylene (PEG)-18-behenylether methacrylate (BEM); and
   iv. about 0.1 wt. % to 10 wt. % of vinylcaprolactam (V-cap);
and wherein the prepared copolymer has a cationic degree of substitution (Cat-DS) of greater than about 0.001 units, and wherein the cationic charge density is in the range of about 1 meq/g to about 6.5 meq/g.

6. The process according to claim 5, wherein the copolymer is prepared by radical polymerization, emulsion polymerization, ionic chain polymerization, bulk polymerization, suspension polymerization or precipitation polymerization.

7. The process according to claim 5, wherein the average molecular weight of the copolymer is in the range of from about 75,000 to 1000,000 g/mol as determined by gel permeation chromatography.

8. A method for washing or caring a keratin substrate comprising applying an effective amount of a personal care composition, wherein the composition comprises the conditioning and/or styling copolymer of claim 1.

9. A method of protecting dyed hair color from fading or wash-out during exposure to air and/or shampooing which comprises contacting/treating said dyed hair with an effective amount a personal care composition, wherein the composition comprises the conditioning and/or styling of claim 1.

* * * * *